US011397187B2

(12) United States Patent
Horsch et al.

(10) Patent No.: US 11,397,187 B2
(45) Date of Patent: Jul. 26, 2022

(54) IGFBP7 FOR PREDICTION OF RISK OF AKI WHEN MEASURED PRIOR TO SURGERY

(71) Applicant: Roche Diagnostics Operations, Inc., Indianapolis, IN (US)

(72) Inventors: Andrea Horsch, Lucern (CH); Birgit Klapperich, Risch (CH); Dirk Block, Bichl (DE); Alfred Engel, Weilheim (DE); Johann Karl, Peissenberg (DE); Rosemarie Kientsch-Engel, Feldafing (DE); Ekaterina Manuilova, Penzberg (DE); Christina Rabe, Bad Heilbrunn (DE); Sandra Rutz, Munich (DE); Monika Soukupova, Wessobrunn (DE); Ursula-Henrike Wienhues-Thelen, Krailling (DE); Peter Kastner, Staffelsee (DE); Edelgard Anna Kaiser, Huennenberg See (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 70 days.

(21) Appl. No.: 15/943,104

(22) Filed: Apr. 2, 2018

(65) Prior Publication Data
US 2018/0231570 A1 Aug. 16, 2018

Related U.S. Application Data

(63) Continuation of application No. PCT/EP2016/074206, filed on Oct. 10, 2016.

(30) Foreign Application Priority Data

Oct. 8, 2015 (EP) ..................................... 15188859

(51) Int. Cl.
*G01N 33/53* (2006.01)
*G01N 33/68* (2006.01)
*G01N 33/74* (2006.01)

(52) U.S. Cl.
CPC ......... *G01N 33/6893* (2013.01); *G01N 33/68* (2013.01); *G01N 33/74* (2013.01); *G01N 2333/47* (2013.01); *G01N 2333/8139* (2013.01); *G01N 2800/347* (2013.01); *G01N 2800/50* (2013.01)

(58) Field of Classification Search
None
See application file for complete search history.

(56) References Cited

U.S. PATENT DOCUMENTS 9,029,093 B2 5/2015 Anderberg et al.
2012/0264148 A1 10/2012 Nezieri et al.

FOREIGN PATENT DOCUMENTS

| CN | 101995428 A | 3/2011 |
|---|---|---|
| EP | 2666872 A1 | 11/2013 |
| JP | 2014-526676 A | 10/2014 |
| WO | 1999/006445 A1 | 2/1999 |
| WO | 2000/070051 A1 | 11/2000 |
| WO | 2005/113585 A2 | 12/2005 |
| WO | 2010/043037 A1 | 4/2010 |
| WO | 2011/157756 A1 | 12/2011 |
| WO | 2013034264 A1 | 3/2013 |
| WO | 2011/073382 A1 | 6/2013 |
| WO | 2014/040759 A1 | 3/2014 |
| WO | 2015/069880 A1 | 5/2015 |

OTHER PUBLICATIONS

Cox et al. Immunoassay Methods, 2012, In: Markossian S, Grossman A, Brimacombe K, et al., editors. Assay Guidance Manual [Internet]. Bethesda (MD): Eli Lilly & Company and the National Center for Advancing Translational Sciences; 2004-.).*
Anderson, Page A. W. et al., Molecular Basis of Human Cardiac Troponin T Isoforms Expressed in the Developing, Adult, and Failing Heart, Circulation Research, 1995, pp. 681-686, vol. 76.
Bartels, H. et al., Serum Kreatininbestimmung Ohne Enteiseissen, Clinica Chimica Acta, 1972, pp. 193-197, vol. 37, English Abstract.
Bauskin, Asne R. et al., The propeptide of macrophage inhibitory cytokine (MIC-1), a TGF-β superfamily member, acts as a quality control determinant for correctly folded MIC-1, The EMBO Journal, 2000, pp. 2212-2220, vol. 19, No. 10.
Bellomo, Rinaldo et al., Acute renal failure—definition, outcome measures, animal models, fluid therapy and Information technology needs: the Second International Consensus Conference of the Acute Dialysis Quality Initiative (ADQI) Group, Critical Care, 2004, pp. R204-R212, vol. 8.
Bootcov, Michelle R. et al., MIC-1, a novel macrophase inhibitory cytokine, is a divergent member of the TGF-β superfamily, Proceedings of the National Academy of Sciences USA, 1997, pp. 11514-11519, vol. 94.

(Continued)

*Primary Examiner* — Christine J Saoud
(74) *Attorney, Agent, or Firm* — Stinson LLP

(57) ABSTRACT

The present disclosure describes a method for predicting the risk of a patient to suffer from acute kidney injury (AKI) during or after a surgical procedure or after administration of a contrast medium. The method is based on the determination of the level of the biomarker IGFBP7 (Insulin-like Growth Factor Binding Protein 7) in a body fluid sample obtained from the patient prior to the surgical procedure or prior to the administration of a contrast medium. Further, the present disclosure describes a method for predicting the risk of a patient to suffer from acute kidney injury (AKI) based on the determination of the amount of the biomarker IGFBP7 (Insulin-like Growth Factor Binding Protein 7) and Cystatin C in a body fluid sample obtained from the patient. The present disclosure further encompasses kits and devices adapted to carry out the methods of the disclosed methods.

12 Claims, 6 Drawing Sheets

(56) References Cited

OTHER PUBLICATIONS

Böttner, Martina et al., Characterization of the rat, mouse, and human genes of growth/differentiation factor-15/macrophage inhibiting cytokine-1 (GDF-15/MIC-1), Gene, 1999, pp. 105-111, vol. 237.
Chan, Lawrence et al., Human Liver Fatty Acid Binding Protein cDNA and Amino Acid Sequence, The Journal of Biological Chemistry, 1985, pp. 2629-2632, vol. 260, No. 5.
Coleman, Matthew D. et al., Preventing acute kidney injury after cardiac surgery, Current Opinion in Anesthesiology, 2011, pp. 70-76, vol. 24.
Cuartero, M. et al., Urinary TIMP2 and IGFBP7 as early biomarkers of acute kidney injury in septic and nonseptic critically ill patients, Critical Care, 2015, p. S102, vol. 19, Supplement 1, Abstract P288.
Ehehalt, K. et al., High normal values of circulating immune cell subsets before surgery may be protective against development of postoperative acute kidney injury, Intensive Care Medicine Experimental, 2015, 2 pp., vol. 3, Supplement 1, A626.
Ferrieres, Gaelle et al., Human cardiac troponin I: precise identification of antigenic epitopes and prediction of secondary structure, Clinical Chemistry, 1998, pp. 487-493, vol. 44, No. 3.
Gaffney, Alan M. and Sladen, Robert N., Acute kidney injury in cardiac surgery, Current Opinion in Anesthesiology, 2015, pp. 50-59, vol. 28, No. 1.
Gandhi, Parul U. et al., Prognostic Usefulness of Insulin-Like Growth Factor-Binding Protein 7 in Heart Failure With Reduced Ejection Fraction: A Novel Biomarker of Myocardial Diastolic Function?, American Journal of Cardiology, 2014, pp. 1543-1549, vol. 114.
Gocze, Ivan et al., Urinary Biomarkers TIMP-2 and IGFBP7 Early Predict Acute Kidney Injury after Major Surgery, PLOS One, 2015, 11 pp., vol. 10, No. 3.
Haase-Fielitz, Anja et al., Neutrophil gelatinase-associated lipocalin as a biomarker of acute kidney injury: a critical evaluation of current status, Annals of Clinical Biochemistry, 2014, pp. 335-351, vol. 51, No. 3.
Hromas, Robert et al., PLAB, a novel placental bone morphogenetic protein, Biochimica et Biophysica Acta, 1997, pp. 40-44, vol. 1354.
Huen, Sarah and Parikh, Chirag R., Predicting Acute Kidney Injury Following Cardiac Surgery: A Systemic Review, Annals of Thoracic Surgery, 2012, pp. 337-347, vol. 93, No. 1.
International Search Report dated Nov. 21, 2016, in Application No. PCT/EP2016/074206, 5 pages.
Kamijo, Atsuko et al., Urinary liver-type fatty acid binding protein as a useful biomarker in chronic kidney disease, Molecular and Cellular Biochemistry, 2006, pp. 175-182, vol. 284.
Kashani, Kianoush et al., Discovery and validation of cell cycle arrest biomarkers in human acute kidney injury, Critical Care, 2013, 12 pps., vol. 17.
Kellum, John A. et al., KDIGO Clinical Practice Guideline for Acute Kidney Injury, Kidney International Supplements, 2012, pp. i-iv, 1-138, vol. 2, No. 1.
Kellum, John A. et al., Section 4: Contrast-induced AKI, Kidney International Supplements, 2012, pp. 69-88, vol. 2, Section 4.
Kiefer, Michael C. et al., The cDNA and derived amino acid sequence for human osteopontin, Nucleic Acids Research, 1989, p. 3306, vol. 17.
Lawton, Lee N. et al., Identification of a novel member of the TGF-beta superfamily highly expressed in human placenta, Gene, 1997, pp. 17-26, vol. 203.
Matsui, Katsuomi et al., Usefulness of Urinary Biomarkers in Early Detection of Acute Kidney Injury After Cardiac Surgery in Adults, Circulation Journal, 2012, pp. 213-220, vol. 76.
McCullough, Peter A., Contrast-Induced Nephropathy Definitons, Epidemiology, and Implications, Interventional Cardiology Clinics, 2014, pp. 357-362, vol. 28, No. 1.
Meersch, Melanie et al., Urinary TIMP-2 and IGFBP7 as Early Biomarkers of Acute Kidney Injury and Renal Recovery following Cardiac Surgery, PLOS One, 2014, e93460, 9 pp., vol. 9, No. 3.
Mehta, Ravindra L. et al., Acute Kidney Injury Network: a report of an initiative to improve outcomes in acute kidney injury, Critical Care, 2007, R31, 8 pages, vol. 11, No. 2.
Motiwala, Shweta R. et al., Measurement of Novel Biomarkers to Predict Chronic Heart Failure Outcomes and Left Ventricular Remodeling, Journal of Cardiovascular Translational Research, 2014, pp. 250-261, vol. 7.
Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.
Paralkar, Vishwas M. et al., Cloning and Characterization of a Novel Member of the Transforming Growth Factor-β/Bone Morphogenetic Protein Family, The Journal of Biological Chemistry, 1998, pp. 13760-13767, vol. 273, No. 22.
Popper, Hans et al., Zur Kreatininbestimmung im Blute, Biochemische Zeitschrift, 1937, pp. 354-357, vol. 291.
Schley, G. et al., Comparative analysis of diagnostic and predictive performance of novel renal biomarkers in plasma and urine of acute kidney injury patients, Intensive Care Medicine Experimental, 2015, p. A258, vol. 3, Suppl 1.
Seelig, H. P. and Wüst, H., Die Kreatinbestimmung mit der Jaffé Reaktion, Ärztliches Labor, 1969, pp. 34-39, English Summary, vol. 15.
Song, Young Rim et al., Prevention of Acute Kidney Injury by Erythropoietin in Patients Undergoing Coronary Artery Bypass Grafting: A Pilot Study, American Journal of Nephrology, 2009, pp. 253-260, vol. 30.
Vives, Marc et al., Cardiac surgery-associated acute kidney injury, Interactive Cardiovascular and Thoracic Surgery, 2014, pp. 637-645, vol. 18.
Yokoyama-Kobayashi, Midori et al., Human cDNA Encoding a Novel TGF-β Superfamily Protein Highly Expressed in Placenta, Journal of Biochemistry, 1997, pp. 622-626, vol. 122, No. 3.
Thakar, Charuhas V. et al., A Clinical Score to Predict Acute Renal Failure after Cardiac Surgery, Journal of the American Society of Nephrology, 2005, pp. 162-168, vol. 16.
Wang, Wang et al., Preoperative serum cystatin C combined with dipstick proteinuria predicts acute kidney injury after cardiac surgery, Renal Failure, 2014, pp. 1497-1503, vol. 36, No. 10.
Wang, Xia and Wang, Jinquan, Biomarkers of acute kidney injury: Pathogenic mechanism and potential therapeutic significance, Journal of Medical Postgraduates, 2015, pp. 318-322, Abstract only, vol. 3.

* cited by examiner

IGFBP7 FOR PREDICTION OF RISK OF AKI WHEN MEASURED PRIOR TO SURGERY

CROSS-REFERENCE TO RELATED APPLICATIONS

This application is a continuation of International Application No. PCT/EP2016/074206 filed Oct. 10, 2016, which claims priority to EP 15188859.1 filed Oct. 8, 2015, all of which are hereby incorporated by reference in their entirety.

BRIEF SUMMARY OF THE DISCLOSURE

The present invention relates to a method for predicting the risk of a patient to suffer from acute kidney injury (AKI) during or after a surgical procedure or after administration of a contrast medium. The method is based on the determination of the level of the biomarker IGFBP7 (Insulin-like Growth Factor Binding Protein 7) in a body fluid sample obtained from the patient prior to said surgical procedure or prior to said administration of a contrast medium. Further, the present invention relates to a method for predicting the risk of a patient to suffer from acute kidney injury (AKI) based on the determination of the amount of the biomarker IGFBP7 (Insulin-like Growth Factor Binding Protein 7) and Cystatin C in a body fluid sample obtained from the patient. The present invention further encompasses kits and devices adapted to carry out the methods of the present invention. Other aspects of the disclosure are evident from the following detailed disclosure, and this summary is not intended to be limiting in any way.

BACKGROUND OF THE DISCLOSURE

Kidney injury represents a complex disorder that occurs in a wide variety of clinical settings, often with serious and fatal complications. Kidney diseases are broadly categorized as chronic kidney disease (CKD) and acute forms of kidney injury. CKD is a chronic disease often resulting from diseases like diabetes, nephropathy, hypertension and cardiovascular diseases.

Acute forms of kidney injury like acute kidney injury (AKI) may occur in individuals after an acute event like an accident, a burn or a trauma. Kidney injury is also a major complication after a surgical intervention or after administration of a contrast medium. Acute kidney injury (AKI) after cardiac surgery confers a significant increased risk of mortality.

Worldwide, over 80 million doses of iodinated contrast media are administered each year, e.g. for angiography or computed tomography, corresponding to approximately 8 million liters. This is one of the highest volumes of medical drugs used. Contrast medium-induced acute kidney injury remains one of the most clinically important complications associated with the administration of contrast media.

The development of AKI after cardiac surgery is independently associated with substantial short and long term morbidity and mortality. AKI develops in up to 30% of patients who undergo cardiac surgery, with up to 3% of patients requiring dialysis (Vives et al., Cardiac surgery—associated acute kidney injury Interactive CardioVascular and Thoracic Surgery 18 (2014) 637-645).

The risk of AKI may be reduced in risk patients e.g. by careful fluid balance before, during and after surgery, avoidance of low cardiopulmonary bypass perfusion temperatures (Kourliouros et al), avoidance or discontinuation of potentially nephrotoxic drugs prior to surgery (Song et al., American Journal of Nephrology 2009, 30: 25). Preoperative strategies to prevent AKI after cardiac surgery include postponing surgery to allow adequate renal recovery after an injury, careful risk stratification, and use of less invasive procedures. Intraoperative strategies to prevent AKI after cardiac surgery include hemodynamic optimization with use of inotropic support and blood transfusion as needed (Coleman et al., 2011, Curr Opin Anesthesiol 24:70-76)

AKI may lead to a number of complications, including metabolic acidosis, high potassium levels, uremia, changes in body fluid balance, and effects to other organ systems. Management of AKI includes supportive care, such as renal replacement therapy, as well as treatment of the underlying disorder. The changes in fluid balance may result in heart failure (or may worsen heart failure). Moreover, it may affect other organ systems. In severe cases of a kidney injury, renal replacement therapy (including e.g. hemodialysis or renal transplantation) may be required. In addition, AKI is associated with increased mortality, greater cost, and prolonged Intensive Care Unit (ICU) and hospital stay.

Acute kidney injury is so far predominantly diagnosed by assessing the serum creatinine level and urine output. An absolute increase in the serum creatinine (SCr) concentration of larger than or equal to 0.3 mg/dL (26.5 µmol/L) from baseline within 48 hours, or a more than 50 percent increase in the serum creatinine, in a period of 7 days, or a urine output of less than 0.5 mL/kg/h for more than 6 hours is indicative for the diagnosis of acute kidney injury. The marker, however, has only limited prognostic value. In addition, the marker is useless in differentiating AKI from CKD when measured only once. Changes in SCr require several hours to days before they reach steady state following an injury to the kidney. Thus, SCr is a late and unspecific marker to define AKI.

The understanding of risk factors is important, in particular in hospitalized patients. Here, the susceptibility should be assessed before certain measures such as surgery or administration of nephrotoxic agents such as contrast agents (KDIGO, Kidney International Supplements (2012)2,69-88). The risk for AKI can be assessed according to clinical scores based on clinical variables and including SCr (Huen S. Parikh C R, Predicting Acute Kidney Injury Following cardiac Surgery: A Systematic Review, Ann Thorac Surg. 2012; 93(1) 337-347).

Haase-Fielitz et al. review the utility of plasma and urine NGAL measurements for the prediction of AKI in humans (Annals of Clinical Biochemistry, 2014, Vol. 51(3) 335-351).

Matsui et al. disclose that urinary L-FABP is a useful biomarker for early detection of AKI and for the prediction of the onset of AKI (Circ J 2012; 76: 213-220).

Meersch et al. investigated whether urine [TIMP-2]*[IGFBP7] (marketed as Nephrocheck®) could predict renal recovery from AKI prior to hospital discharge (PLoS ONE 9(3): e93460. doi:10.1371/journal.pone.0093460). According to Meersch, urinary TIMP2 and IGFBP7 were not observed to be suited for prediction of acute kidney injury and renal recovery before surgery.

WO 2010/043037 describes IGFBP7 as a biomarker for cancer.

EP 2 666 872 A1 discloses various markers for the diagnosis and prognosis of renal injury and renal failure. One of the disclosed markers is IGFBP7. The marker can be determined in a body fluid such as urine or plasma. Examples 1 and 2 deal with AKI after administration of a contrast medium and after surgery, respectively.

Motiwala et al. disclose IGFBP7 as a marker to predict chronic heart failure outcomes (J. of Cardiovasc. Trans. Res. DOI 10.1007/s12265-013-9522-8). No information about future AKI is provided.

Gandhi et al. disclose IGFBP7 as a prognostic biomarker for heart failure with reduced ejection fraction (Am J Cardiol 2014; 114:1543e1549).

Median IGFBP7 concentrations (ng/mL) at different times (pre-surgery, 4 and 24 hours after surgery) are provided for the subgroup without CKD with (n=10/50, black boxes) and without AKI (n=40/50, white boxes).

Figure 4A:
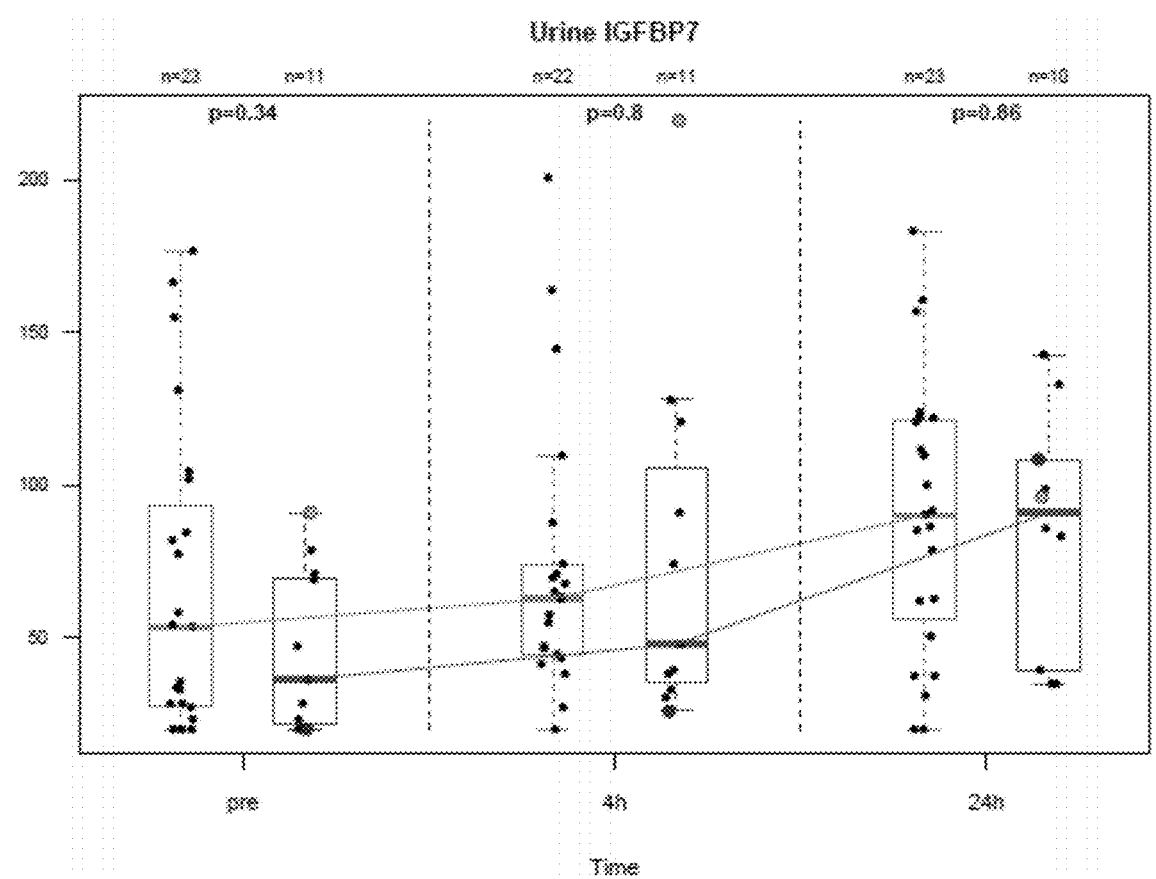

FIG. 4A IGFBP7 levels in cardiac surgery patients in urine samples. The marker was determined in a subgroup of 34 patients more details, see Example 4).

Figure 4B:
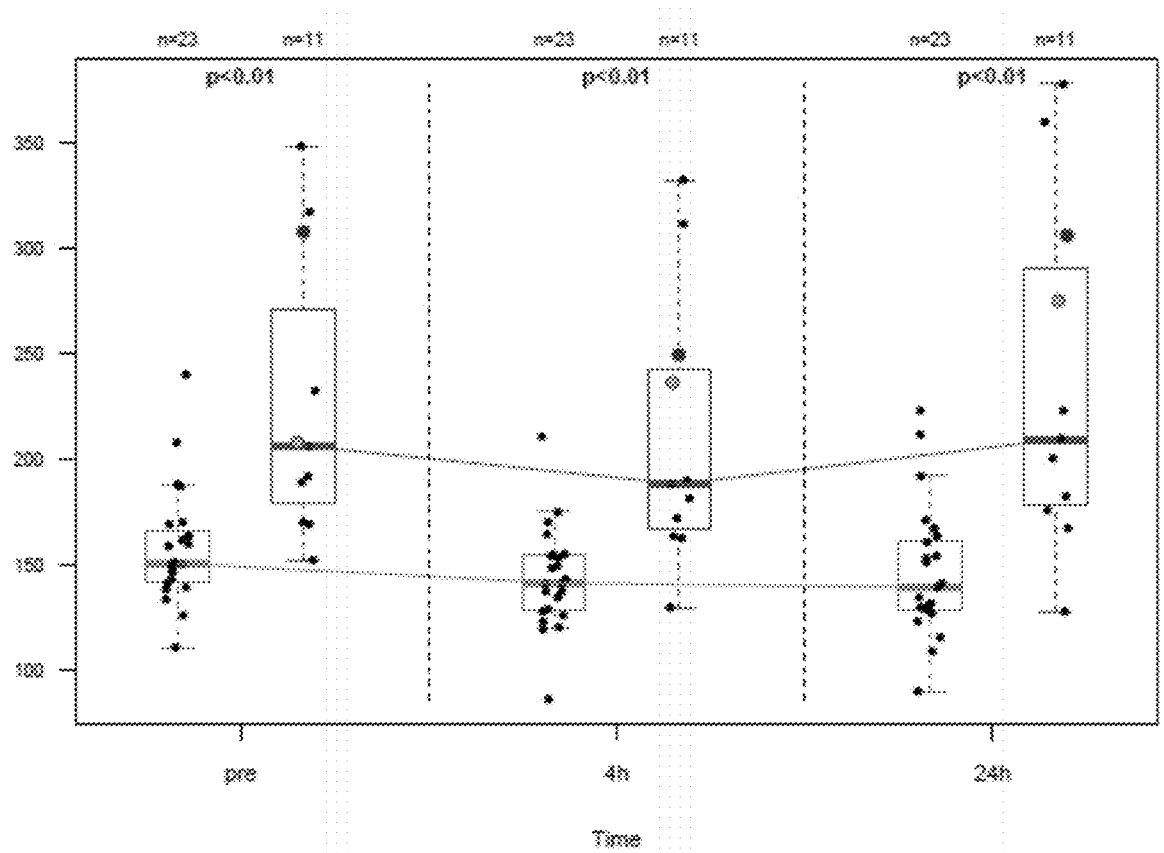

FIG. 4B IGFBP7 levels in cardiac surgery patients in plasma samples. The marker was determined in a subgroup of 34 patients (for more details, see Example 4)

Figure 5:
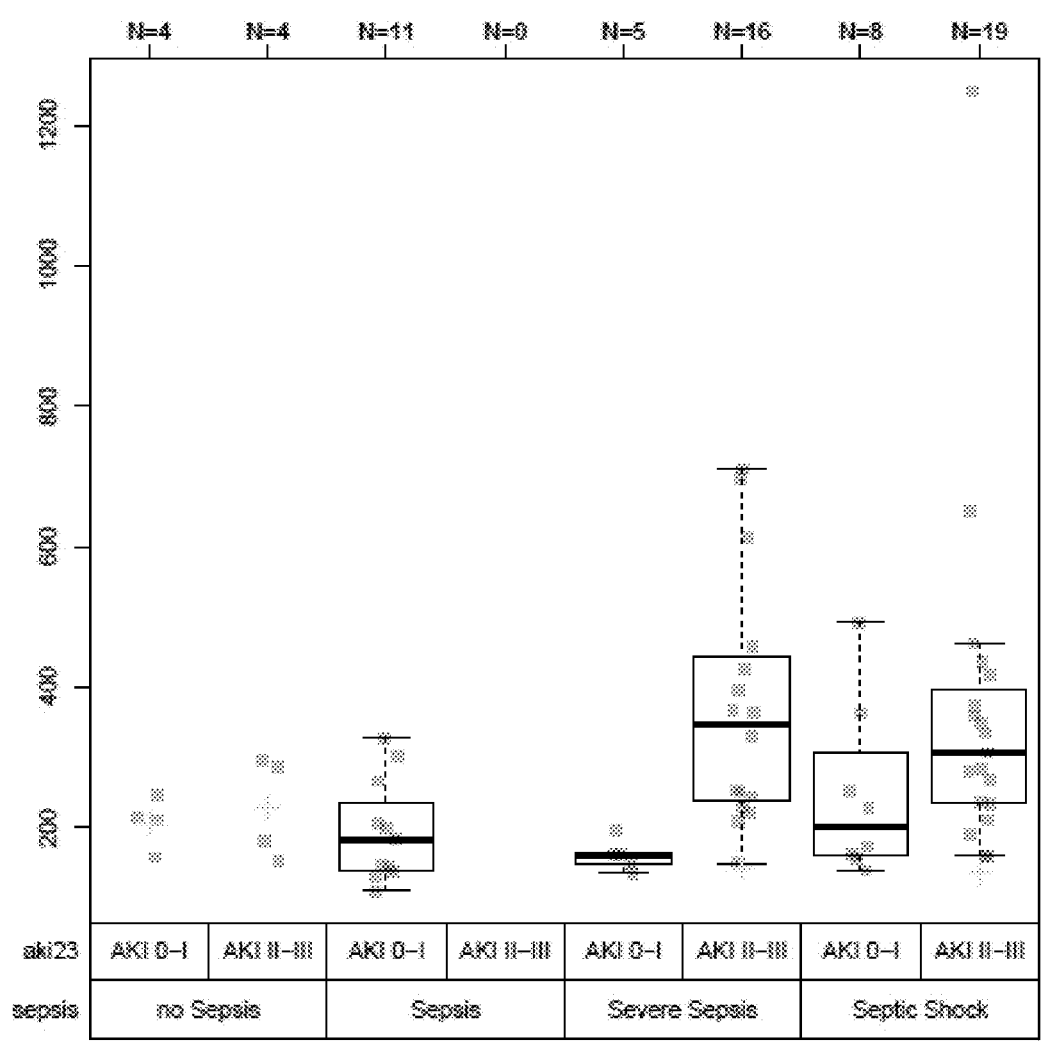

FIG. 5: Plasma IGFBP7 levels were determined in 67 ICU patients and median concentrations (ng/mL) are provided for several subgroups of patients with different severity of sepsis and different AKI stages.

DETAILED DESCRIPTION OF THE DISCLOSURE

There is a high need of identifying individuals at risk of AKI before surgery or before administration of a contrast medium to avoid risk factors that might lead to the precipitation of acute kidney injury. Moreover, in these individuals careful follow up of kidney function after surgery or after administration of a contrast medium is indicated.

Consequently, the technical problem underlying the present invention could be seen as the provision of means and methods for predicting the risk of a patient to suffer from kidney injury after a surgical procedure. The problem is solved by the embodiments of the present invention described in the claims and in the specification below.

Advantageously, it was shown in the context of the studies underlying the present invention that IGFBP7 is a reliable biomarker for predicting the intra- or post-operative risk of a patient to suffer from AKI in a blood, serum, or plasma sample that has been obtained from the patient prior to a surgical procedure. Thus, the biomarker provides valuable information and thus a basis for treatment decisions at an early time point.

Accordingly, the present invention relates to a method for predicting the risk of a patient to suffer from acute kidney injury (AKI) during or after a surgical procedure or to suffer from acute kidney injury (AKI) after administration of a contrast medium, said method comprising the steps of:
a) determining the amount of the biomarker IGFBP7 (Insulin-like Growth Factor Binding Protein 7) in a blood, serum or plasma sample obtained from the patient prior to said surgical procedure or prior to said administration of a contrast medium, and
b) comparing the determined amount of said biomarker to a reference.

Preferably, the risk of the patient to suffer from acute kidney injury during or after a surgical procedure or after administration of a contrast medium is predicted by carrying out the further step of c) predicting the risk of the patient to suffer from acute kidney injury during or after a surgical procedure or to suffer from acute kidney injury (AKI) after administration of a contrast medium based on the result of the comparison carried out in step b).

In a preferred embodiment, the risk of a patient to suffer from acute kidney injury (AKI) during or after a surgical procedure is predicted. In this case, the amount of the biomarker as referred to in step (a) is determined in a blood, serum or plasma sample obtained from the patient prior to said surgical procedure.

Accordingly, the present invention in particular relates to a method for predicting the risk of a patient to suffer from acute kidney injury (AKI) during or after a surgical procedure, said method comprising the steps of:
a) determining the amount of the biomarker IGFBP7 (Insulin-like Growth Factor Binding Protein 7) in a blood, serum or plasma sample obtained from the patient prior to said surgical procedure, and
b) comparing the determined amount of said biomarker to a reference.

In a preferred embodiment, the risk of a patient to suffer from acute kidney injury (AKI) after administration of a contrast medium is predicted. In this case, the amount of the biomarker as referred to in step (a) is determined in a blood, serum or plasma sample obtained from the patient prior to said administration of said contrast medium.

Accordingly, the present invention relates to a method for predicting the risk of a patient to suffer from acute kidney injury (AKI) after administration of a contrast medium, said method comprising the steps of:
a) determining the amount of the biomarker IGFBP7 (Insulin-like Growth Factor Binding Protein 7) in a blood, serum or plasma sample obtained from the patient prior to said administration of a contrast medium, and
b) comparing the determined amount of said biomarker to a reference.

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a), (b) and/or (c) may in total or in part be assisted by automation, e.g., by a suitable robotic and sensory equipment for the determination in step (a), or a computer-implemented comparison and/or prediction based on said comparison in step (b).

The term "predicting the risk" as used herein refers to assessing the probability according to which a patient will suffer from acute kidney injury i) during or within a certain predictive window after a surgical procedure or ii) within a certain predictive window after administration of a contrast medium. The term, preferably, relates to predicting whether or not there is a risk of acute kidney injury during or after a surgical procedure, or after administration of a contrast medium. The actual prediction may comprise further steps such as the confirmation of the prediction. Thus, the term "predicting" in the context of the present invention preferably encompasses aiding the physician to predict the risk of a patient to suffer from acute kidney injury A patient who is at risk of acute kidney injury during or after a surgical procedure, or after administration of a contrast medium preferably has an elevated risk as compared to the average risk (of suffering from acute kidney injury i. during or after a surgical procedure, or ii. after administration of a contrast medium) in a population of patients. A patient who is not at risk of acute kidney injury during or after a surgical procedure, or after administration of a contrast medium preferably has a reduced risk as compared to the average risk (of suffering from acute kidney injury i. during or after a surgical procedure, or ii. after administration of a contrast medium) in a population of patients. As will be understood by those skilled in the art, such an assessment is usually not intended to be correct for 100% of the patients to be investigated. The term, however, requires that prediction can be made for a statistically significant portion of patients in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction of an elevated, average or decreased risk will be correct for at least 60%, at least 70%, at least 80%, or at least 90% of the patients of a given cohort or population.

The term "predicting the risk of acute kidney injury during or after a surgical procedure" as used herein means that the patient to be analyzed by the method of the present invention is allocated either into the group of patients being at risk of acute kidney injury during or after a surgical procedure, or into the group of patients being not at risk of acute kidney injury during or after a surgical procedure. The term "predicting the risk of acute kidney injury after administration of a contrast medium" as used herein means that the patient to be analyzed by the method of the present invention is allocated either into the group of patients being at risk of acute kidney injury after administration of a contrast medium, or into the group of patients being not at risk of acute kidney injury after administration of a contrast medium. A risk of acute kidney injury during or after a surgical procedure (or after administration of a contrast medium) as referred to in accordance with the present invention, preferably, means that the risk of acute kidney injury during or after a surgical procedure (or after administration of a contrast medium) is increased (within the predictive window). Preferably, said risk is increased as compared to the average risk in a cohort of patients (i.e. in a group of patients that will undergo a surgical procedure, or in a group of patients that will receive a contrast medium). If a patient is not at risk of acute kidney injury during or after a surgical procedure (or after administration of a contrast medium) as referred to in accordance with the present invention, preferably, the risk of acute kidney injury during or after a surgical procedure (or after administration of a contrast medium) shall be reduced (within the predictive window). Preferably, said risk is reduced as compared to the average risk in a cohort of patients (i.e. a group of patients that will undergo a surgical procedure, or in a group of patients a group of patients that will receive a contrast medium). It is to be understood that a patient who is not at risk of AKI as defined herein, may nevertheless suffer from AKI. However, the risk is relatively low, in particular as compared to a patient who is at risk.

A patient who is at risk of acute kidney injury during or after a surgical procedure preferably has a risk of 25% or larger, or, more preferably of 30%, or larger, most preferably of 35% or larger of acute kidney injury during or after a surgical procedure, preferably, within a predictive window of one week after the surgical procedure. A patient who is not at risk of acute kidney injury during or after a surgical procedure preferably has a risk of lower than 15%, more preferably of lower than 10% or lower of acute kidney injury during or after a surgical procedure, preferably, within a predictive window of one week after the surgical procedure. A patient who is at risk of acute kidney injury after administration of a contrast medium preferably has a risk of 15% or larger, or, more preferably of 25% or larger of acute kidney injury after administration of a contrast medium, preferably, within a predictive window of one week after administration of a contrast medium. A patient who is not at risk of acute kidney injury after administration of a contrast medium preferably has a risk of lower than 8%, more preferably of lower than 5% or lower of acute kidney injury after administration of a contrast medium, preferably, within a predictive window of one week after administration of a contrast medium.

In a preferred embodiment of the present invention, the risk of acute kidney injury during or after a surgical procedure shall be predicted. Thus, the risk of a patient who will undergo a surgical procedure is predicted to suffer from intra-operative AKI (i.e. to suffer from AKI during the procedure), or post-operative AKI (i.e. AKI after said surgical procedure). The term "during a surgical procedure" is well known in the art. Preferably, the term encompasses the period/interval between the first incision and the completion of the surgery. The term "after surgical procedure", preferably means "immediately after the surgical procedure", in particular "immediately after completion of the surgical procedure". "Immediately after" preferably means within about 3 hours, about 6 hours, about 12 hours, about 1 day, about 2 days, about 3 days, about 4 days, about 5 days, about 6 days or, in particular within about 1 week after the surgical procedure, in particular after completion of the surgical procedure. In accordance with the present invention, the predictive window after the procedure thus is preferably a period of about 3 hours, about 6 hours, about 12 hours, about 1 day, about 2 days, about 3 days, about 4 days, about 5 days, about 6 days or in particular about 1 week after the surgical procedure, in particular after completion of the surgical procedure.

In another preferred embodiment of the present invention, the risk of acute kidney injury after administration of a contrast medium shall be predicted. Thus, the risk of a patient who will receive a contrast medium is predicted to suffer from AKI after administration of said contrast medium. The term "after administration of a contrast medium", preferably means "immediately after administration of a contrast medium. "Immediately after" in this context preferably means within about 12 hours, about 24 hours, in particular about 48 hours, about 3 days, or about 5 days after administration of a contrast medium. In a preferred embodiment, the term means "within about 48 hours after administration of a contrast medium". In a particular preferred embodiment, the term means "within about three days after administration of a contrast medium". In another preferred embodiment, the term means "within about five days after administration of a contrast medium". In accordance with the present invention, the predictive window after administration of a contrast medium thus is preferably a period of about 12 hours, about 24 hours, about 48 hours, about 3 days, or about 5 days after administration of a contrast medium.

However, it is in particular envisaged that the predictive window is not more than two weeks, in particular not more than one week after the surgery, in particular after completion of the surgical procedure or is not more than two weeks, in particular not more than about one week, in particular than about five days after administration of a contrast medium. Thus, the present invention does not envisage the prediction of a long-term risk to suffer from AKI.

Preferably, the term "about" as used herein encompasses a range of + and −20% relative to the specific value, amount, concentration, time period etc., e.g., indication of a value of "about 100" is meant to encompass a value of a numerical range of 100+/−20%, i.e. a value range from 80 to 120. Preferably, the term encompasses a range of + and −10% relative to the specific value, amount, concentration, time period etc. and, more preferably, a range of + and −5% relative to the specific value, amount, concentration, time period etc. Most preferably, the term "about" refers to the exact value, amount, concentration, time period, etc.

The term "patient" or "subject" as used herein relates to an animal, in particular a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the patient or subject is human. The terms "patient" and "subject" are interchangeably used herein.

In a preferred embodiment, the patient according to the present invention, preferably, shall undergo surgical procedure after the sample to be tested has been obtained. Thus, the patient shall be subjected to a surgical procedure after said the sample has been obtained.

In another preferred embodiment, the patient according to the present invention, preferably, shall receive a contrast medium after the sample to be tested has been obtained. Thus, a contrast medium shall be administered to the patient after said the sample has been obtained.

In a preferred embodiment, the patient does not require treatment in an intensive care unit at the time at which the sample is obtained. Thus, the patient is preferably not an intensive care unit patient at the time at which the sample is obtained.

The term "intensive care unit" is known in the art. Preferably, the term refers to a health care unit that treats patients with life-threatening conditions which require constant support from equipment and medication in order to maintain normal bodily functions.

In addition, it is envisaged that the patient is not a trauma and/or burn patient. Thus, the patient to be tested shall not suffer from burn injury and/or trauma (at the time at which the sample is obtained).

It is to be understood that the patient may be admitted to an intensive care unit after completion of the surgical procedure (or after administration of the contrast medium).

In a preferred embodiment, the patient to be tested suffers from chronic kidney disease (in particular at the time at which the sample is obtained). In another preferred embodiment, the patient to be tested does not suffer from chronic kidney disease (in particular at the time at which the sample is obtained).

In a preferred embodiment of the present invention, the risk of a patient to suffer from AKI during or after a surgical procedure shall be predicted. The term "surgical procedure" as used in the context of the present invention, preferably, refers to any surgery that involves anesthesia and/or mechanical ventilation, in particular anesthesia and mechanical ventilation. Preferably, the anesthesia is localized anesthesia, more preferably, the anesthesia is general anesthesia.

The term "surgical procedure", preferably, includes interventions on inner organs (in particular on the liver, kidney, bowel, stomach, lung, without being exhaustive) as long as it involves anesthesia and/or mechanical ventilation. Preferably, the term "surgical procedure" also includes trauma surgery and burn surgery as long as it involves anesthesia and/or mechanical ventilation. In particular, the term includes interventions on the heart (in particular, on the valve or any part of the myocard) that involves anesthesia and/or mechanical ventilation. Thus, the surgical procedure is, preferably, cardiac surgery.

Cardiac surgery is, preferably, valve surgery, and more preferably coronary artery bypass graft (CABG) surgery (frequently also referred to as "aortocoronary bypass" or "coronary artery bypass surgery"). CABG is indicated if a patient suffers from stenosis of the coronary arteries which cannot be treated successfully with other methods such as percutaneous coronary intervention (PCI). This is typically the case if multiple vessels are affected or if the stenosis is not clearly localized. In this surgery, arteries or veins are grafted to the coronary arteries. Thereby, it is possible to bypass atherosclerotic narrowing and improve the blood supply to the myocardium. CABG is either performed "on-pump" i.e. the heart is stopped and does not beat during surgery, or "off-pump", i.e. the heart continues to beat during the procedure. It is particularly preferred that CABP is performed "on-pump". This surgery preferably encompasses the cardiopulmonary bypass (CPB), a technique that temporarily takes over the function of the heart and lungs during surgery, maintaining the circulation of blood and the oxygen content of the body. The CPB pump itself is often referred to as a heart-lung machine. Further preferred is a bypass of obstructed coronary vessels using vessels preferably veins from other parts of the body (preferably the legs) or an implantation of the arteria thoracica interna into the heart to bridge obstructed vessels or to provide additional blood supply to the heart.

In another preferred embodiment of the present invention, the risk of a patient to suffer from AKI after administration of a contrast medium shall be predicted. The term "contrast medium" is known by the skilled person. The term, preferably, relates to any substance that is deemed appropriate, when administered to a subject, to increase the contrast, preferably, in X-ray imaging by affecting the attenuation of X-rays, and, therefore, to enhance the visibility of structures and fluids. Thus, a contrast medium, preferably, enables differentiation of certain parts of the body from surrounding areas which are of similar density. Preferably, a contrast medium in the context with the present invention is an opaque or a positive contrast medium, i. e. a contrast medium that has a higher attenuation density than the surrounding tissue and, therefore, an increased absorption of x-rays. Positive contrast media are well known in the art and include, preferably, non iodine based contrast media and, more preferably, iodine based contrast media, i.e. iodinated contrast media. Examples of non iodine based and iodine based contrast media are known by the skilled person. Iodine based contrast media in the context of the present invention, preferably, encompass water insoluble, oily, and more preferably water-soluble iodine based contrast media. Oily iodine based contrast media, preferably, are lipiodol, ethiodol and ethyl esters of iodinated fatty acids of poppy seeds which can be used for lymphography as well as for hysteroalpingography, or iodophylundecyclic acid (iophendylat, Pantopaque, Myodil) which can be used for mylography. Water-soluble iodine based contrast media in the context of the present invention are, preferably, derivatives of tri-iodinated benzoic acid. Derivatives of tri-iodinated benzoic acid are referred to as monomeric when they contain only one benzene ring, and dimeric when they contain two benzene rings. Preferably, the monomeric and the dimeric contrast media as contemplated by the present invention are ionic or, more preferably, non ionic. Most preferably, the contrast medium is a monomeric, non ionic contrast medium such as Iobitridol (Xenetix).

Typically, non ionic contrast media do not dissociate and their water-solubility is due to hydrophilic hydroxyl groups. Monomeric ionic media are salts that dissociate into two molecules, one anion containing the radiopaque property due to three iodine atoms, and one cation without radiopaque properties. They encompass, preferably, oral cholegraphic contrast media and contrast media for urography/angiography. Preferably, monomeric ionic contrast media are ioglicate (Rayvist), iodamide (Uromiro), acetrizoate (Diaginol, Urokon) diatrizoate (Angiografin, Hypaque, Renografin, Urografin, Urovison), metrizoate (Isopaque, Triosil). A variety of different non ionic monomeric contrast media is known in the art. They, preferably, encompass (Amipaque), iohexol (Omnipaque), iopamidol (Iopamiro), iopentol (Imagopaque), iopromide (Ultravist), ioversol (Optiray).

Dimeric iodine based contrast media, preferably, comprise two tri-iodinated benzene rings. They can be grouped in ionic intravenous cholegraphic contrast media, monoacidic ionic contrast media and non ionic contrast media. Dimeric iodinated contrast media are, preferably, sodium meglumine ioxaglate (Hexabrix), iotrolan (Isovist), iodixanol (Visipaque).

Non iodine contrast media frequently contain barium, mainly in form of insoluble barium sulfate. They are, preferably, administered for examining the gastrointestinal tract (e.g. in form of the so called "barium meal" "barium swallow" or in enema form).

The contrast media may be administered by any method deemed appropriate. The person skilled in the art knows that the method to be selected for administration may depend on the contrast medium and/or the purpose of the examination for which the contrast medium is administered. Preferably, contrast media based on barium are administered by swallowing or in enema form. Contrast media based on iodine are, preferably, administered by injection into the veins, the spinal canal, or the arteries. Also contemplated is the use of a catheter in order to administrate an iodine based contrast medium.

Preferably, the administration of a contrast medium, particularly, of an iodine based contrast medium, is for computed tomography, and, most preferably, for angiography. Further contemplated by the present invention is the administration of a suitable contrast medium for ultrasonic examination or magnetic resonance imaging (MRI).

The term "acute kidney injury" or "AKI" is well known in art. As used herein, the term preferably refers to a rapid loss of kidney function. Preferably, said rapid loss of kidney function is caused by damage to the kidney(s). AKI can be a post-renal, intrinsic or, pre-renal injury of the kidney. The endpoint of acute kidney injury within said window will become apparent, e.g. by an increase of the serum creatinine as defined elsewhere in this specification. The criteria for diagnosing and classifying AKI are based on changes in serum creatinine (SCr) and urine output (UO). The term is defined in the KDIGO guidelines which are herewith incorporated by reference in their entirety (KDIGO, Kidney International Supplements (2012)2,69-88), Preferably, AKI during or immediately after a surgical procedure is characterized by an increase of serum creatinine of at least 0.3 mg/dl within 48 hours or by an increase of at least 50% from a baseline sample (preferably within 48 hours after surgery). Preferably, AKI begins during the surgical procedure or not later than one week after surgery (or not later than one week, in particular not later than 5 days after administration of a contrast medium). Depending on the diagnostic method applied it may only be recognizable several days after onset.

Preferred methods and criteria to diagnose AKI have been described in Bellomo et al. (Crit Care, 2004, 8(4), R204-12), Mehta et al. (Crit Care. 2007; 11(2): R31), and in the KDIGO Clinical Practice Guideline for Acute Kidney Injury (Kidney International, 2012, 2(1), 1-138) all of which are herewith incorporated with respect to their entire disclosure content, in particular with respect to the AKI criteria. Historically, the RIFLE criteria were used to classify AKI. The RIFLE criteria are disclosed in in Bellomo. The AKI Network (AKIN) subsequently modified the RIFLE criteria. The AKIN criteria are described in Mehta et al.

More recently, the KDIGO (Kidney Disease: Improving Global Outcomes) classification system for AKI was introduced to harmonize these two previous systems (see Clinical Practice Guideline for Acute Kidney Injury).

In a preferred embodiment, the AKI to be predicted is AKI according to the RIFLE criteria (see Bellomo et al.). The RIFLE acronym represents increasing severity class: Risk, Injury, Failure, Loss of function, and End-stage renal disease. Severity is defined by the worst of the two criteria (i.e. SCr or UO). Changes in SCr and UO are measured over a 7-day period.

In an even further preferred embodiment, the AKI to be predicted is AKI according to the AKIN criteria (see Mehta et al.). According to the AKIN criteria, AKI is characterized by an increase within 48 hours in SCr of larger than 0.3 mg/dL or a more than 1.5-fold increase in SCr from baseline value, or a urine output of less than 0.5 mL/kg/h for more than 6 hours. The AKIN criteria were applied in the studies underlying the present invention.

In another preferred embodiment, the AKI to be predicted is AKI according to the KDIGO criteria (Kidney International, 2012, 2(1), 1-138). The KDIGO system is based on RIFLE and AKIN criteria. KDIGO criteria for diagnosing AKI incorporate both the absolute increase in SCr of ≥0.3 mg/dL within 48 hours from AKIN, and the 1.5-fold increase within 7 days from RIFLE. According to the KDIGO criteria, AKI is characterized by:

Increase in SCr of ≥0.3 mg/dL within 48 hours; or
Increase in SCr of ≥1.5 times from baseline (i.e. an increase of more than or equal to 1.5 fold as compared to the baseline level); or
Urine output of <0.5 mL/kg/h for 6 hours.

An AKI that is associated with the administration of a contrast medium is preferably characterized by an increase of serum creatinine of at least 0.5 mg/dl within 48 hours or at least 25% from baseline within 48 hours after administration of a contrast medium.

In the context of the studies carried out in connection with the present invention it has been shown that the determination of IGFBP7 in a blood, serum or plasma sample allows for a reliable prediction of AKI independent of the severity, i.e. mild, moderate and severe AKI can be predicted. Thus, the term "AKI" as used herein preferably encompasses mild, moderate and severe AKI.

In a preferred embodiment, the AKI to be predicted is mild AKI.

In another preferred embodiment, the AKI to be predicted is moderate AKI.

In another preferred embodiment, the AKI to be predicted is severe AKI.

A mild AKI is preferably AKI stage I according to the AKIN criteria.

A moderate AKI is preferably AKI stage II according to the AKIN criteria.

A severe AKI is preferably AKI stage III according to the AKIN criteria.

The criteria for AKI stage I, II and III are summarized in Table 2 of the publication Mehta.

According to the AKIN criteria, AKI stage I is characterized by an increase in SCr of larger than 0.3 mg/dL or an 1.5 to 2-fold increase in SCr from baseline value, or a urine output of less than 0.5 mL/kg/h for more than 6 hours.

According to the AKIN criteria, AKI stage II is characterized by a 2- to 3 fold increase in SCr from baseline, or a urine output of less than 0.5 mL/kg/h for more than 12 hours.

According to the AKIN criteria, AKI stage III is characterized by an increase in SCr (Serum Creatinine) of larger than or equal to 4.0 mg/dL or a more than 3-fold increase in SCr from base-line value, or a urine output of less than 0.3 mL/kg/h for 24 hours or anuria for 12 hours or more.

It is to be understood that the AKI during or after said surgical procedure, or after administration of a contrast medium shall be associated with the surgical procedure and with the administration of the contrast medium. The term "associated with" as used herein, preferably, refers to a temporal and, in particular, a causal relationship between the surgical procedure and the AKI and between the administration of a contrast medium and the AKI, respectively. The person skilled in the art understands what is meant if AKI is considered to be associated with a surgical procedure or administration of a contrast medium (see KDIGO Section 4 Contrast-induced AKI p69 ff, Kidney International Supplements (2012) 2,69-88). In particular, the AKI shall be considered to be associated with a surgical procedure, if the AKI has been caused by said surgical procedure, i.e. is the consequence of said surgical procedure (In other words, the AKI to be predicted shall not occur if no surgical procedure would be carried out). Likewise, the AKI shall be considered to be associated with the administration of a contrast medium, if the AKI has been caused by said administration of the contrast medium, i.e. is the consequence of the administration (In other words, the AKI to be predicted shall not occur if no contrast medium would be administered) Indication for such causal connection is e.g. a close time-relationship as well as a close statistical relationship between said surgical procedure or said administration of the contrast medium and the incidence of AKI. In particular, the AKI shall be associated with said surgical procedure, if the AKI arises/occurs during or immediately after a surgical procedure. Moreover, the AKI shall be associated with said administration of a contrast medium, if the AKI arises/occurs immediately after administration of the contrast medium.

The sample in the context of the present invention shall be a blood, serum or plasma sample. In a preferred embodiment, the sample has been obtained from the patient prior to the surgical procedure, i.e. before the patient undergoes the surgical procedure. In another preferred embodiment, the sample has been obtained from the patient prior to the administration of the contrast medium, i.e. before the patient receives the contrast medium. Usually, the sample has been obtained on the day preceding the (scheduled) surgical procedure or the administration of the contrast medium. However, it is contemplated the sample has been obtained within four weeks (i.e. within a period of four weeks) prior to the surgical procedure or the administration of the contrast medium. In a preferred embodiment, the sample has been obtained within up to one week prior to the surgical procedure (or the administration of the contrast medium). In another preferred embodiment the sample has been obtained, within three days prior to the surgery (or the administration of the contrast medium). Further, it is contemplated that the sample has been obtained within 12 hours prior to the surgery (or the administration of the contrast medium). Preferably, the aforementioned time periods are (back) calculated from the first incision of the surgical procedure (if the risk to suffer from AKI during or after a surgical procedure is predicted).

Preferably, the sample has been obtained prior to a hydration, in particular an intravenous hydration, that precedes the surgical procedure.

The term "determining" (herein also referred to as "measuring") the amount of a biomarker as referred to herein refers to the quantification of the biomarker, e.g. to determining the amount of the biomarker in the sample, employing appropriate methods.

The biomarkers to be determined in connection with the present invention are protein biomarkers. How to determine the amount, and thus how to determine the amount of a protein biomarker is well known in the art and is e.g. described in WO 2014/040759 which is herewith incorporated by reference in its entirety, see in particular page 15, line 15, to page 19 line 25.

In an embodiment, the amount of the at least one biomarker is determined by contacting the sample with a binding agent that specifically binds to the respective marker, thereby forming a complex between the agent and said marker, detecting the amount of complex formed, and thereby determining the amount of said marker.

Preferably, the binding agent binds specifically to a biomarker as referred to herein. Preferred binding agents include antibodies, nucleic acids, peptides or polypeptides such as receptors or binding partners for the peptide or polypeptide and fragments thereof comprising the binding domains for the peptides, and aptamers, e.g. nucleic acid or peptide aptamers, in particular antibodies. Antibodies as referred to herein include both polyclonal and monoclonal antibodies, as well as fragments thereof, such as Fv, Fab and F(ab)2 fragments that are capable of binding to the biomarker. The present invention also includes single chain antibodies and humanized hybrid antibodies wherein amino acid sequences of a non-human donor antibody exhibiting a desired antigen-specificity are combined with sequences of a human acceptor antibody. The term "specific binding" or "specifically binds" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule. Preferably, the amount of binding to a molecule other than the target molecule results in a binding affinity which is only 10% or less, more preferably only 5% or less of the affinity to the target molecule.

Third, the binding agent may be coupled covalently or non-covalently to a label allowing detection and determination of the binding agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent.

In step a) of the method of the present invention, the amount of Insulin-like Growth Factor Binding Protein 7(=IGFBP7) shall be determined. Preferably, the amount of the IGFBP7 protein is determined. IGFBP7 is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). Preferably, the term "IGFBP7" refers to human IGFBP7. The sequence of the protein is well known in the art and is e.g. accessible via GenBank (NP_001240764.1).

In a preferred embodiment of the method of the present invention, the method further comprises (in step a)) the determination of the amount(s) of at least one further biomarker selected from the group consisting of Cystatin C, L-FABP (liver-type fatty acid binding protein), Osteopontin, IL-6 (Interleukin 6), GDF-15 (Growth Differentiation Factor 15), NGAL, a cardiac Troponin and a BNP-type peptide in the blood, serum or plasma sample obtained from the patient prior to said surgical procedure. Preferably, the determined amount(s) is (are) compared to a reference (in step b)). Based on the comparison, the risk of AKI during or after the surgical procedure is predicted.

Thus, the present invention envisages a method for predicting the risk of a patient to suffer from acute kidney injury (AKI) during or after a surgical procedure or to suffer from acute kidney injury (AKI) after administration of a contrast medium, comprising the steps of:

a) determining the amounts of the biomarker IGFBP7 and of at least one further biomarker selected from the group consisting of Cystatin C, L-FABP (liver-type fatty acid binding protein), Osteopontin, IL-6 (Interleukin 6), GDF-15 (Growth Differentiation Factor 15), NGAL, a cardiac Troponin, Creatinine and a BNP-type peptide in a blood, serum or plasma sample obtained from the patient prior to said surgical procedure or prior to said administration of a contrast medium, and b) comparing the amounts as determined in step (a) to a reference.

The definitions given herein above apply mutatis mutandis.

Preferably, the risk of the patient to suffer from acute kidney injury during or after a surgical procedure or after administration of a contrast medium is predicted by carrying out the further step of c) predicting the risk of the patient to suffer from acute kidney injury during or after a surgical procedure or to suffer from acute kidney injury (AKI) after administration of a contrast medium based on the result of the comparison carried out in step b).

Cystatin C is a small, 13 kDa, protein that is produced by virtually all nucleated cells. Its production rate is constant and is unaffected by inflammatory process, gender, age and muscle mass. In the normal kidney, Cystatin C is freely filtered at the globular membrane and then nearly completely reabsorbed and degraded by the proximal tubular cells. Therefore, the plasma concentration of Cystatin C is almost exclusively determined by the glomerular filtration rate (GFR), making Cystatin C an indicator of GFR. Cystatin C has advantages over routine clinical measures of renal function. It is more accurate than plasma creatinine, the Cockcroft-Gault estimation of creatinine clearance and is more reliable than the 24-h creatinine clearance. Cystatin C has been shown to increase earlier than serum creatinine in patients developing AKI, preferably one to two days earlier than serum creatinine.

The term "liver-type fatty acid binding protein" (L-FABP), preferably, relates to a polypeptide being a liver type fatty acid binding protein. The L-FABP protein is derived from the human FABP1 gene. Liver-type fatty acid binding protein is an intracellular carrier protein of free fatty acids that is expressed in the proximal tubules of the human kidney. Kamijo et al. (Urinary liver-type fatty acid binding protein as a useful biomarker in chronic kidney disease. Mol. Cell Biochem. 2006; 284) reported that urinary excretion of L-FABP may reflect various kind of stresses that cause tubulointerstitial damage and may be a useful clinical marker of the progression of chronic renal disease. For a sequence of human L-FABP, see e.g., Chan et al.: Human liver fatty acid binding protein cDNA and amino acid sequence. Functional and evolutionary implications J. Biol. Chem. 260 (5), 2629-2632 (1985) or GenBank Acc. Number M10617.1.

Osteopontin (OPN), also known as bone sialoprotein I (BSP-1 or BNSP), early T-lymphocyte activation (ETA-1), secreted phosphoprotein 1 (SPP1), 2ar and Rickettsia resistance (Ric), is a polypeptide which is a highly negatively charged, extracellular matrix protein that lacks an extensive secondary structure. It is composed of about 300 amino acids (297 in mouse; 314 in human) and is expressed as a 33-kDa nascent protein; there are also functionally important cleavage sites. OPN can go through posttranslational modifications which increase its apparent molecular weight to about 44 kDa. The sequence of osteopontin is well known in the art (human osteopontin: UniProt P10451, GenBank NP_000573.1). The human OPN protein and cDNA have been isolated and sequenced (Kiefer M. C, et al., Nucl. Acids Res. 17 (1989) 3306).

Interleukin-6 (abbreviated as IL-6) is an interleukin secreted by T cells and macrophages to stimulate immune response, e.g. during infection and after trauma, especially burns or other tissue damage leading to inflammation. It acts as both a pro-inflammatory and anti-inflammatory cytokine. In humans, it is encoded by the IL6 gene. The sequence of human IL-6 is well known in the art and can be assessed e.g. via GenBank (see NM_000600.3 for the polynucleotide sequence, and NP_000591.1 for the amino acid sequence). IL-6 signals through a cell-surface type I cytokine receptor complex consisting of the ligand-binding IL-6Rα chain (CD126), and the signal-transducing component gp130 (also called CD130). CD130 is the common signal transducer for several cytokines including leukemia inhibitory factor (LIF), ciliary neurotropic factor, oncostatin M, IL-11 and cardio-trophin-1, and is almost ubiquitously expressed in most tissues.

The term "cardiac Troponin" refers to all Troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac Troponin refers to Troponin T and/or Troponin I, and, most preferably, to Troponin T. It is to be understood that isoforms of Troponins may be determined in the method of the present invention together, i.e. simultaneously or sequentially, or individually, i.e. without determining the other isoform at all. Amino acid sequences for human Troponin T and human Troponin I are disclosed in Anderson, loc cit and Ferrieres 1998, Clinical Chemistry, 44: 487-493.

The BNP-type peptide (Brain Natriuretic Peptide-type peptide) is preferably selected from the group consisting of pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-proBNP) and the active hormone (BNP). Preferably, BNP-type peptide according to the present invention is BNP, more preferably the BNP-type peptide is NT-proBNP. BNP is the active hormone and has a shorter half-life than its respective inactive counterpart NT-proBNP.

The marker "creatinine" is well known in the art. The term, preferably, refers to serum creatinine (SCr). In muscle metabolism, creatinine is synthesized endogeneously from creatine and creatine phosphate. Under conditions of normal renal function, creatinine is excreted by glomerular filtration. Creatinine determinations are performed for the diagnosis and monitoring of acute and chronic renal disease as well as for the monitoring of renal dialysis. Creatinine concentrations in urine can be used as reference values for the excretion of certain analytes (albumin, α-amylase). Creatinine can be determined as described by Popper et al., (Popper H et al. Biochem Z 1937; 291:354), Seelig and Wüst (Seelig H P, Wüst H. Arztl Labor 1969; 15:34) or Bartels (Bartels H et al. Clin Chim Acta 1972; 37:193). For example, sodium hydroxide and picric acid are added to the sample to start the formation of creatinine-picric acid complex. In alkaline solution, creatinine forms a yellow-orange complex with picrate. The color intensity is directly proportional to the creatinine concentration and can be measured photometrically.

"Growth-Differentiation Factor-15" (abbreviated GDF-15) is a polypeptide which is member of the transforming growth factor (TGF)-β cytokine superfamily. GDF-15 was originally cloned as macrophage-inhibitory cytokine-1 and later also identified as placental transforming growth factor-β, placental bone morphogenetic protein, non-steroidal anti-inflammatory drug-activated gene-1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-β-related cytokines, GDF-15 is synthesized as an inactive precursor protein, which undergoes disulfide-linked homodimerization. Upon proteolytic cleavage of the N-terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111).

The marker NGAL (neutrophil gelatinase-associated lipocalin) is known in the art. It is a protein that in humans is encoded by the LCN2 gene. NGAL levels in patients with AKI have been associated with the severity of their prognosis and can be used as a biomarker for AKI.

The at least one further marker can be determined in the same blood, serum or plasma sample or in a different blood, serum or plasma sample.

The term "amount" as used herein encompasses the absolute amount of a biomarker as referred to herein, the relative amount or concentration of the said biomarker as well as any value or parameter which correlates thereto or can be derived therefrom.

The term "comparing" as used herein refers to comparing the amount of the biomarker in the sample from the individual or patient with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. The value of the measured or detected amount of the biomarker in the sample from the individual or patient and the reference amount can be, e.g., compared to each other and the said comparison can be automatically carried out by a computer program executing an algorithm for the comparison.

In an embodiment, the further biomarker(s) is (are) selected from the group consisting of L-FABP, CystatinC, Creatinine, Osteopontin, NTproBNP, cardiac Troponin and IL6. Preferably, the further biomarker(s) are selected from Cystatin C, Osteopontin, L-FABP and NT-proBNP.

In a preferred embodiment, the further biomarker is L-FABP. Thus, the method of the present invention comprises the combined determination of IGFBP7 and L-FABP. In another preferred embodiment, the method of the present invention comprises the combined determination of IGFBP7 and Cystatin C. In another preferred embodiment, the method of the present invention comprises the combined determination of IGFBP7 and Creatinine. In another preferred embodiment, the method of the present invention comprises the combined determination of IGFBP7 and Osteopontin. In another preferred embodiment, the method of the present invention comprises the combined determination of IGFBP7 and NT-proBNP. In another preferred embodiment, the method of the present invention comprises the combined determination of IGFBP7 and a cardiac Troponin. In another preferred embodiment, the method of the present invention comprises the combined determination of IGFBP7 and IL-6. In another preferred embodiment, the method of the present invention comprises the combined determination of IGFBP7 and GDF-15. In another preferred embodiment, the present invention comprises the combined determination of IGFBP7, Cystatin C, NT-proBNP, Osteopontin, and L-FABP. In another preferred embodiment, the method of the present invention comprises the combined determination of IGFBP7 and IL-6. In another preferred embodiment, the method of the present invention comprises the combined determination of IGFBP7 and NGAL.

The method of the present invention comprises the step of comparing the amount of the biomarker(s) as determined in step to a reference. The term "reference" is well known in the art.

Preferably, the term "reference" refers to "reference amount". The term "reference amount" is well known in the art as well. Preferred reference amounts can be determined by the skilled person without further ado. Preferably, the term "reference amount" herein refers to a predetermined value for the respective biomarker. In this context, the term "amount" encompasses the absolute amount, the relative amount or concentration as well as any value or parameter which correlates thereto or can be derived therefrom. In a preferred embodiment, the reference amount is an amount which allows for allocating the patient into a group of patients who are at risk of acute kidney injury during or after a surgical procedure, or into a group of patients who are not at risk of acute kidney injury during or after a surgical procedure. In another preferred embodiment, the reference amount is an amount which allows for allocating the patient into a group of patients who are at risk of acute kidney injury after administration of a contrast medium, or into a group of patients who are not at risk of acute kidney injury after administration of a contrast medium. Thus, the reference amount shall allow for differentiating between a patient who is at risk or who is not at risk (of acute kidney injury i. during or after a surgical procedure, or ii. after administration of a contrast medium).

The skilled artisan will appreciate the reference amount is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference amount meeting those requirements. In one embodiment the reference amount is determined in a reference sample or samples from a patient (or group of patients) who are at risk of acute kidney injury during or after a surgical procedure or after administration of a contrast medium. In another embodiment, the reference is determined in a reference sample or samples from a patient (or group of patients) who are not at risk (of acute kidney injury during or after a surgical procedure, or after administration of a contrast medium). In certain embodiments the reference amount can e.g. be set to any percentage between 25% and 75% of the overall distribution of the values in a risk entity investigated. In other embodiments the reference amount can e.g. be set to the median, tertiles or quartiles as determined from the overall distribution of the values in reference samples from a risk entity investigated. In one embodiment the reference amount is set to the median value as determined from the overall distribution of the values in a risk entity investigated. The reference amount may vary depending on various physiological parameters such as age, gender or subpopulation, as well as on the means used for the determination of the biomarkers referred to herein. In one embodiment, the reference sample is the same type of sample from the individual or patient subjected to the method of the invention. Thus, the reference sample shall be a blood, serum or plasma sample. E.g. if according to the invention plasma is used as a sample to determine the amount of biomarkers in the individual, the reference amount is also determined in plasma thereof.

Preferably, the following applies as algorithm.

Preferably, an amount of the biomarker IGFBP7 above the reference indicates that the patient is at risk of acute kidney injury during or after a surgical procedure (or after administration of a contrast medium), whereas an amount of the biomarker IGFBP7 below the reference indicates that the patient is not at risk of acute kidney injury during or after a surgical procedure (or after administration of a contrast medium). This applies e.g. if the reference is a predetermined value. Preferably, the reference is a reference amount.

Preferably, the following applies as algorithm if a combination of biomarkers is determined (such as IGFBP7 and L-FABP):

Preferably, amounts of the biomarkers above the respective reference indicate that the patient is at risk of acute kidney injury during or after said surgical procedure (or after administration of a contrast medium), whereas amounts of the biomarkers below the respective reference indicate that the patient is not at risk of acute kidney injury during or after said surgical procedure (or after administration of a contrast medium). This applies e.g. if the references are predetermined values. Preferably, the references are reference amounts.

Preferably, an individual reference (amount) is used for each of the biomarkers, if more than one biomarker is determined (such as IGFBP7 and L-FABP).

In particular, if the reference is an amount of the respective biomarker in a patient or group of patients known to have suffered from acute kidney injury during or after a surgical procedure (or after administration of a contrast medium), the following applies:

Preferably, an essentially identical or increased amount (essentially identical or increased amounts) of the biomarker(s) as compared to said reference amount(s) indicate(s) that the patient is at risk of acute kidney injury during or after a surgical procedure (or after administration of a contrast medium).

In particular, if the reference is an amount of the respective biomarker in a patient or group of patients known not to have suffered from acute kidney injury during or after a surgical procedure (or after administration of a contrast medium), the following applies:

Preferably, an essentially identical or decreased amount (essentially identical or decreased amounts) of the biomarker(s) as compared to said reference amount(s) indicate(s) that the patient is not at risk of acute kidney injury during or after a surgical procedure (or after administration of a contrast medium).

In certain embodiments, the term "larger than the reference amount" or "above the reference amount" refers to an amount of the biomarker in the sample from the individual or patient above the reference amount or to an overall increase of 5%, 10%, 20%, 25%, 30%, 40%, 50%, 60%, 70%, 80%, 85%, 90%, 95%, 100% or greater, determined by the methods described herein, as compared to the reference amount. In certain embodiments, the term increase refers to the increase in biomarker amount in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference amount, e.g. predetermined from a reference sample. In certain embodiments, the term "lower than the reference amount" or "below" herein refers to an amount of the biomarker in the sample from the individual or patient below the reference amount or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference amount. In certain embodiments, the term decrease in biomarker amount in the sample from the individual or patient wherein the decreased amount is at most about 0.9-, 0.8-, 0.7-, 0.6-, 0.5-, 0.4-, 0.3-, 0.2-, 0.1-, 0.05-, or 0.01-fold of the reference amount, e.g. predetermined from a reference sample, or lower.

The following additional steps can be carried out, if the risk of the subject to suffer from AKI during or after a surgical procedure is predicted:

In a preferred embodiment of the method of the present invention, said method further comprise the step of recommending and/or initiating at least one measure, if it is predicted that the patient is at risk of AKI during or after a surgical procedure. Thus, the present invention further relates to a method of recommending or initiating a measure. The measure to be recommended or initiated shall be any measure which aims at reducing the risk of AKI during or after surgical procedure. In an embodiment, said measure is a treatment which aims at reducing the risk of AKI during or after surgical procedure.

The recommendation or initiation is preferably based on steps a) and b) of the method of the present invention.

Preferably, the least one measure to be recommended or initiated, if the patient is at risk to suffer from AKI during or after a surgical procedure, is selected from
- discontinuation and/or avoidance of nephrotoxic agents
- ensuring volume status and perfusion pressure,
- avoiding hyperglycemia,
- avoiding radiocontrast measures In addition, the at least one measure is selected from:
- restriction of protein intake
- avoiding the administration of diuretics
- avoiding the administration of aminoglycosides Pre-operative measures to reduce the risk of AKI include postponing the surgical procedure to allow adequate renal recovery and/or to elect less invasive procedures. Intra-operative measures (i.e. measures carried out during the surgical procedure) to reduce the risk of AKI after the procedure include hemodynamic optimization with use of inotropic support and/or blood transfusion as needed.

Further, it is envisaged to monitor the blood pressure once the prediction of a risk of acute kidney injury has been made. In case of increased blood pressure, blood pressure lowing medicaments shall be administered, or in case of decreased blood pressure, blood pressure increasing methods or drugs shall be applied.

The following additional steps can be carried out, if the risk of the subject to suffer from AKI after administration of a contrast medium is predicted:

In a preferred embodiment of the method of the present invention, said method further comprise the step of recommending and/or initiating at least one measure, if it is predicted that the patient is at risk of AKI after administration of a contrast medium. Thus, the present invention further relates to a method of recommending or initiating a measure. The measure to be recommended or initiated shall be any measure which aims at reducing the risk of AKI after administration of a contrast medium. In an embodiment, said measure is a treatment which aims at reducing the risk of AKI after administration of a contrast medium.

The recommendation or initiation is preferably based on steps a) and b) of the method of the present invention.

Preferably, the least one measure to be recommended or initiated, if the patient is at risk to suffer from AKI after administration of a contrast medium, is selected from
- administration of lowest possible dose of contrast medium, and
- administration of iso-osmolar or low-osmolar iodinated contrast medium, and preferably avoiding high-osmolar iodinated contrast medium In addition, the at least one measure is selected from:
- restriction of protein intake
- considering alternative imaging methods,
- i.v. volume expansion with either isotonic sodium chloride or sodium bicarbonate solutions,
- administration oral N-acetylcysteine, preferably together with i.v. isotonic crystal-loids.

The definitions given herein above in connection with the method of the present invention preferably apply mutatis mutandis to the following.

The present invention also relates to the i) use of the biomarker IGFBP7, and optionally, of at least one biomarker selected from the group of Cystatin C, L-FABP (liver-type fatty acid binding protein), Osteopontin, IL-6 (Interleukin 6), NGAL, GDF-15 (Growth Differentiation Factor 15), Creatinine, a cardiac Troponin and a BNP-type peptide or the ii) use of at least one detection agent for the biomarker IGFBP7 and optionally of at least one detection agent for a biomarker selected from the group of Cystatin C, L-FABP (liver-type fatty acid binding protein), Osteopontin, IL-6 (Interleukin 6), NGAL, GDF-15 (Growth Differentiation Factor 15), Creatinine, a cardiac Troponin and a BNP-type peptide in a blood, serum, or plasma sample obtained from a patient prior to a surgical procedure or prior to a administration of a contrast medium for predicting the risk of a patient to suffer from acute kidney injury (AKI) during or after a surgical procedure, or after administration of a contrast medium.

The term "detection agent" is well known in the art. If the biomarker is a polypeptide or peptide, in particular if the biomarker is IGFBP7, Cystatin C, L-FABP (liver-type fatty acid binding protein), Osteopontin, IL-6 (Interleukin 6), NGAL, GDF-15 (Growth Differentiation Factor 15), Creatinine, a cardiac Troponin or a BNP-type peptide, the detection agent preferably specifically binds to said marker. A preferred detection agent is an antibody which specifically binds to the biomarker to be determined. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Preferably, the antibody is a polyclonal antibody. More preferably, the antibody is a monoclonal antibody. Another binding agent that can be applied, in an aspect, may be an aptamere which specifically binds to the at least one marker in the sample. The term "specific binding" or "specifically binds", when referring to a nucleic acid aptamer as a binding agent, refers to a binding reaction wherein a nucleic acid aptamer binds to the corresponding target molecule with an affinity in the low nM to pM range. In yet an aspect the, sample is removed from the complex formed between the binding agent and the at least one marker prior to the measurement of the level of formed complex. Accordingly, in an aspect, the binding agent may be immobilized on a solid support. In yet an aspect, the sample can be removed from the formed complex on the solid support by applying a washing solution. The formed complex shall be proportional to the amount of the at biomarker present in the sample.

If the biomarker is creatinine, the detection agent may be picric acid which forms a complex with creatinine.

Further, a device adapted for carrying out the method of the present invention is provided, said device comprising
  a) an analyzer unit comprising a detection agent for determining the amount of IGFBP7 (and optionally at least one further detection agent for determining the amount of a biomarker selected from the group of Cystatin C, L-FABP (liver-type fatty acid binding protein), Osteopontin, NGAL, IL-6 (Interleukin 6), GDF-15 (Growth Differentiation Factor 15), Creatinine, a cardiac Troponin and a BNP-type peptide) in a blood, serum, or plasma sample obtained from a patient prior to a surgical procedure or prior to a administration of a contrast medium, and
  b) an analyzer unit for comparing the determined amount (s) with a reference amount(s), whereby the risk of a patient to suffer from acute kidney injury (AKI) during or after a surgical procedure, or after administration of a contrast medium, is predicted, said unit comprising a database with a reference amount (or amounts) and a computer-implemented diagnostic algorithm for carrying out the comparison.

Preferred reference levels and diagnostic algorithms are disclosed elsewhere herein.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electro-magnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Further, an analyzer unit of the system may include one or more incubation units (for example, for maintaining a sample or a reagent at a specified temperature or temperature range). In embodiments, an analyzer unit may include a thermocycler, include a real-time thermocycler, for subjecting a sample to repeated temperature cycles and monitoring a change in the level of an amplification product with the sample.

Further, the invention pertains to a kit adapted for carrying out a method of the present invention comprising a detection agent for determining the amount of IGFBP7 (and optionally at least one further detection agent for determining the amount of a biomarker selected from the group of Cystatin C, L-FABP (liver-type fatty acid binding protein), Osteopontin, IL-6 (Interleukin 6), NGAL, GDF-15 (Growth Differentiation Factor 15), Creatinine, a cardiac Troponin and a BNP-type peptide) in a blood, serum, or plasma sample obtained from a patient prior to a surgical procedure or prior to a administration of a contrast medium, a reference standard or reference standard(s) as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above, i.e. a solution with a pre-defined level for the biomarker as referred to herein representing a reference level.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein). For example, the kits may include an antibody that is labelled with a fluorophore or an antibody that is a member of a fusion protein. In the kit, the probe may be immobilized, and may be immobilized in a specific conformation. For example, an immobilized probe may be provided in a kit to specifically bind target protein, to detect target protein in a sample, and/or to remove target protein from a sample.

The present invention further concerns a method of aiding in the prediction of the risk of a patient to suffer from acute kidney injury during or after a surgical procedure, or to suffer from acute kidney injury (AKI) after administration of a contrast medium, said method comprising the steps of:
  a) obtaining a sample, preferably a blood, serum or plasma sample from a subject as referred to above in connection with the method for predicting the risk of a patient to suffer from acute kidney injury,
  b) determining the amount of the biomarker IGFBP7 and optionally the amount of at least one further biomarker selected from the group of Cystatin C, L-FABP (liver-type fatty acid binding protein), Osteopontin, IL-6 (Interleukin 6), NGAL, GDF-15 (Growth Differentiation Factor 15), Creatinine, a cardiac Troponin and a BNP-type peptide in said sample, and c) providing information on the determined amount of the biomarker IGFBP7 and optionally on the determined amount of the at least one further biomarker to the attending physician of the subject, thereby aiding in the in the prediction of the risk of the patient to suffer from acute kidney injury during or after a surgical procedure, or to suffer from acute kidney injury (AKI) after administration of a contrast medium.

The attending physician shall be the physician who requested the determination of the biomarker(s). The aforementioned method shall aid the attending physician in the prediction of the risk of the patient to suffer from acute kidney injury. Thus, the method does not encompass the actual prediction.

Step a) of the aforementioned method of obtaining the sample does not encompass the drawing of the sample from the subject. Preferably, the sample is obtained by receiving a sample from said subject. Thus, the sample can have been delivered.

The present invention further relates to a method, preferably of aiding in the prediction of the risk of a patient to suffer from acute kidney injury during or after a surgical procedure, or to suffer from acute kidney injury (AKI) after administration of a contrast medium, comprising:

a) providing a test for the biomarker IGFBP7 and optionally a test at least one further biomarker selected from the group of Cystatin C, L-FABP (liver-type fatty acid binding protein), Osteopontin, IL-6 (Interleukin 6), NGAL, GDF-15 (Growth Differentiation Factor 15), Creatinine, a cardiac Troponin and a BNP-type peptide, and b) providing instructions for using of test results obtained or obtainable by said test(s) in a blood, serum or plasma sample of a patient in the prediction the risk of the patient to suffer from AKI during or after a surgical procedure, or to suffer from acute kidney injury (AKI) after administration of a contrast medium.

The purpose of the aforementioned method is, preferably, the aid in the in the prediction of the risk of a patient to suffer from acute kidney injury.

The instructions shall contain a protocol for carrying out the method for predicting the risk of the patient to suffer from acute kidney injury as described herein above. Further, the instructions shall contain at least one value for a reference amount for IGFBP7 and optionally at least one value for a reference amount for the at least one further biomarker.

The "test" is preferably a kit adapted to carry out the method of prediction the risk of AKI as described elsewhere. The term "Kit" is explained herein below. E.g. said kit shall comprise at least one detection agent for the biomarker IGFBP7 and optionally at least one detection agent for the at least one further biomarker. The detection agents for the biomarkers can be provided in a single kit or in separate kits.

The test result obtained or obtainable by said test, is the value for the amount of the biomarker(s).

Prediction of Acute Kidney Injury based on the Combined Determination of the Amount of IGFBP7 and Cystatin C.

The definitions provided in connection with the prediction of AKI after surgery or administration of a contrast medium preferably apply to the following embodiments of the present invention.

Advantageously, it has been shown in the context of the studies underlying the present invention that the combined determination of the biomarkers IGFBP7 and Cystatin C allows for a reliable prediction of AKI in a subject.

Accordingly, the present invention further relates to a method for predicting the risk of a patient to suffer from acute kidney injury (AKI), comprising the steps of:

a) determining the amount of the biomarker IGFBP7 (Insulin-like Growth Factor Binding Protein 7) and the amount of Cystatin C in a body fluid sample obtained from the patient, and b) comparing the determined amounts of said biomarker to at least one reference.

In a preferred embodiment, the risk of a patient to suffer from acute kidney injury (AKI) after administration of a contrast medium is predicted. In this case, the amount of the biomarker as referred to in step (a) is determined in a blood, serum or plasma sample obtained from the patient prior to said administration of said contrast medium.

Preferably, the risk of the patient to suffer from acute kidney injury is predicted by carrying out the further step of c) predicting the risk of the patient to suffer from acute kidney injury based on the result of the comparison carried out in step b.

As forth herein in connection with the method for predicting the risk of a patient to suffer from acute kidney injury (AKI) during or after a surgical procedure of the present invention, the method is preferably, is an ex vivo or in vitro method. The same applies to the aforementioned method.

The term "predicting the risk" as used herein refers to assessing the probability according to which a patient will suffer from acute kidney injury within a certain predictive window after the sample has been obtained. The term, preferably, relates to predicting whether or not there is a risk of acute kidney injury. The actual prediction may comprise further steps such as the confirmation of the predicting. Thus, the term "predicting" in the context of the present invention preferably encompasses aiding the physician to predict the risk of a patient to suffer from acute kidney injury. A patient who is at risk of acute kidney injury preferably has an elevated risk as compared to the average risk (of suffering from acute kidney injury) in a population of patients. A patient who is not at risk of acute kidney injury during or after a surgical procedure, or after administration of a contrast medium preferably has a reduced risk as compared to the average risk (of suffering from acute kidney injury) in a population of patients.

The term "predicting the risk of acute kidney injury during or after a surgical procedure" as used herein means that the patient to be analyzed by the method of the present invention is allocated either into the group of patients being at risk of acute kidney injury.

Preferably, the predictive window to be applied in connection with the abovementioned method is a period of about 6 hours, about 12 hours, about 1 day, about 2 days, about 3 days, about 4 days, about 5 days, about 6 days or in particular about 1 week, preferably after the sample to be tested has been obtained. In preferred embodiment, said period is a period of about 1 day. In another preferred embodiment, said period is a period of about three days.

The term "patient"/"subject" has been defined above. The definition applies, preferably, accordingly. In addition to the definition above, it is contemplated by the above method that the patient can be a patient who is not undergoing a surgery and/or who is not receiving a contrast medium.

In a preferred embodiment of the aforementioned method of the present invention, the patient is a sepsis patient. The term sepsis is well known in the art. The term preferably refers to a systemic inflammatory response syndrome (SIRS) which is caused by an infection. Symptoms of sepsis are preferably fever, increased heart rate, increased breathing rate, and confusion. Sepsis is caused by an immune response triggered by an infection. An "infection" in the sense of the present invention preferably is a viral, fungus or bacterial infection, preferably a bacterial infection associated with bacteria selected from *E coli, staphylococcus aureus, Klebsiella pneumoniae, Streptococci* or *Pseudomonas aeroginosa*. The infection may as well be an infection by a fungus selected from *Candida albicans, Candida tropicalis* or *Aspergillus fumigatus*. An infection is diagnosed on the basis of assays and criteria generally known to the physician. Preferably, the infection is diagnosed on the basis of a bacterial culture assay, e.g. a culture medium inoculated with a sample from the patient, or based on molecular diagnostic methods. A fungus infection may for example be determined based on the generally known test assays such as Septifast.

The term "sepsis" preferably encompasses all stages of sepsis. In particular, the term encompasses severe sepsis and septic shock. Severe sepsis is sepsis associated with insufficient organ function or insufficient blood flow. Insufficient blood flow may be evident by low blood pressure, high blood lactate, or low urine output. Patients with septic shock have low blood pressure due to sepsis that does not improve after administration of intravenous fluids.

In accordance with the aforementioned method a sepsis patient is preferably a patient who suffers from sepsis when the sample is obtained. However, it is also envisaged that the sepsis patient does not suffer from sepsis at the time at which the sample is obtained but will suffer from sepsis after the sample is obtained. Preferably, the sepsis patient suffers from sepsis with one week, or in particular within three days after the sample has been obtained.

In an embodiment of the above mentioned method, the subject is an intensive care unit patient at the time at which the sample is obtained.

The sample to be tested in accordance with the aforementioned method is preferably a body fluid. In a preferred embodiment, said sample is urine. In another preferred embodiment, said sample is blood, serum or plasma.

In a preferred embodiment, the patient to be tested suffers from chronic kidney disease (in particular at the time at which the sample is obtained). In another preferred embodiment, the patient to be tested does not suffer from chronic kidney disease (in particular at the time at which the sample is obtained).

The aforementioned method comprises the determination of the amounts of two markers, IGFBP7 and Cystatin C. The markers are determined elsewhere herein. Preferably, said amounts are compared to reference amounts. Thus, it is envisaged that that the amount of IGFBP7 is compared to reference amount and the amount of Cystatin C is compared to a reference amount. Preferably, increased amounts of the two markers as compared to the reference amounts are indicative for a subject who is a risk of AKI. Also preferably, decreased amounts of the two markers as compared to the reference amounts are indicative for a subject who is a not risk of AKI.

In a preferred embodiment of the aforementioned method of the present invention, said method further comprise the step of recommending and/or initiating at least one measure, if it is predicted that the patient is at risk of AKI. Such measures are described elsewhere herein.

The present invention further concerns a method of aiding in the prediction of the risk of a patient to suffer from acute kidney injury, said method comprising the steps of:
a) obtaining a sample, preferably a blood, serum or plasma sample from a subject as referred to herein in connection with the aforementioned method for predicting the risk of a patient to suffer from acute kidney injury,
b) determining the amount of the biomarker IGFBP7 and the amount of Cystatin C, in said sample, and
c) providing information on the determined amount of the biomarker IGFBP7 and on the determined amount of Cystatin C to the attending physician of the subject, thereby aiding in the in the prediction of the risk of the patient to suffer from acute kidney injury.

For the definitions, see also the abovementioned method of aiding in the prediction of the risk of a patient to suffer from acute kidney injury.

The present invention further relates to a method, preferably of aiding in the prediction of the risk of a patient to suffer from acute kidney injury, comprising:
a) providing a test for the biomarker IGFBP7 and a test for the biomarker Cystatin C, and
b) providing instructions for using of test results obtained or obtainable by said tests in a blood, serum or plasma sample of a patient in the prediction the risk of the patient to suffer from AKI.

The present invention also relates to the i) use of the biomarker IGFBP7, and of the biomarker Cystatin C or the ii) use of at least one detection agent for the biomarker IGFBP7 and of at least one detection agent for the biomarker Cystatin C in a body fluid sample obtained from a patient predicting the risk of a patient to suffer from acute kidney injury (AKI). The definitions above apply accordingly.

All references referred to above are herewith incorporated by reference with respect to their entire disclosure content as well as their specific disclosure content explicitly referred to in the above description.

EXAMPLES

The following Examples shall illustrate the invention. They shall, however, not be construed as limiting the scope of the invention.

Example 1

Association Circulating IGFBP7 Levels with AKI in the Perioperative Setting

Figure 1:
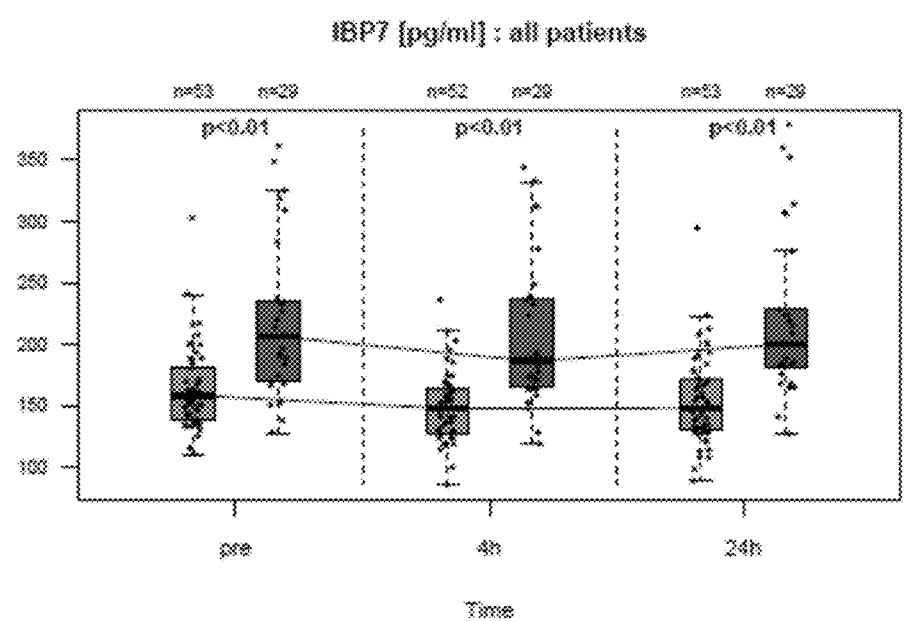
FIG. 1 IGFBP7 levels in 82 unselected adults undergoing cardiac surgery on the day before surgery as well as 4 and 24 hours after completion of CBP (which was defined as time point 0). Postoperative AKI within 3 days of surgery as defined by Acute Kidney Injury Network serum creatinine criteria were recorded within 3 days of surgery in 29 cases. Median IGFBP7 concentrations (ng/mL) at different times (pre-surgery, 4 and 24 hours after surgery) are provided for patients with (n=29/82, black boxes) and without AKI (n=53/82, white boxes).

The association of circulating IGFBP7 levels with AKI was investigated in patients undergoing cardiac surgery using cardiopulmonary bypass (CPB) at the University Hospital Erlangen. Patients with end stage renal disease, previous kidney transplantation and immunosuppressive medication were excluded. Patients who developed AKI after surgery had significantly higher plasma IGFBP7 levels versus non-AKI patients at all points in time investigated (see Table 1). Pre-operative IGFBP7 for the entire cohort had a median value of 167 ng/ml. Pre-operative IGFBP7 was elevated in patients with AKI vs. No AKI (206 vs. 158). IGFBP7 was also significantly elevated in patients with AKI at every time point post-operatively (4-hours and 24-hours) (FIG. 1).

Conclusion:

The absolute IGFBP7 biomarker values show good prognostic performance even before surgery, as well as 4 h and 24 h after surgery.

TABLE 1

IGFBP7 levels in patients undergoing cardiac surgery with versus without AKI Plasma levels of IGFBP7, Creatinine, Cystatine C, L-FABP and Osteopontin were measured in 82 unselected adults undergoing cardiac surgery on the day before surgery as well as 4 and 24 hours after completion of CBP (which was defined as time point 0). Postoperative AKI within 3 days of surgery as defined by Acute Kidney Injury Network serum creatinine criteria were recorded within 3 days of surgery in 29 cases. Median IGFBP7 concentrations (ng/mL) at different times (pre-surgery, 4 and 24 hours after surgery) are provided for all study subjects as well as for the subgroups with and without AKI. Out of the 29 patients, 26 had AKI stage I, 1 AKI stage II and 2 AKI stage III. All stages could be predicted including AKI stage I, i.e. a mild form of AKI.

| | IGFBP7 median concentration (ng/mL) | | |
|---|---|---|---|
| Time of sampling | All | No AKI (n = 53) | AKI (n = 29) |
| Pre-surgery | 167 (110-361) | 158 (110-301) | 206 (128-361) |
| 4 hrs after surgery | 158 (86-343) | 148 (86-236) | 186 (119-343) |
| 24 hrs after surgery | 167 (89-378) | 148 (89-295) | 200 (127-378) |

Example 2

Association of Circulating IGFBP7 with AKI in Subgroups with and without Preexisting CKD The association of circulating IGFBP7 to AKI was investigated also in subgroups of patients undergoing cardiac surgery with versus without preexisting chronic CKD. 32/82 (39%) of observed patients had diagnosed CKD. The subgroup of patients with preexisting CKD had a higher proportion of AKI patients versus the subgroup without CKD (59% versus 20%) as demonstrated in Table 2.

Plasma levels of IGFBP7 were determined in association to AKI in cardiac surgery patients before and at 4 and 24 hours after surgery. In the subgroup of patients with preexisting CKD 19/32 patients developed AKI. In the subgroup of patients of patients without CKD 10/40 developed AKI.

Figure 2:
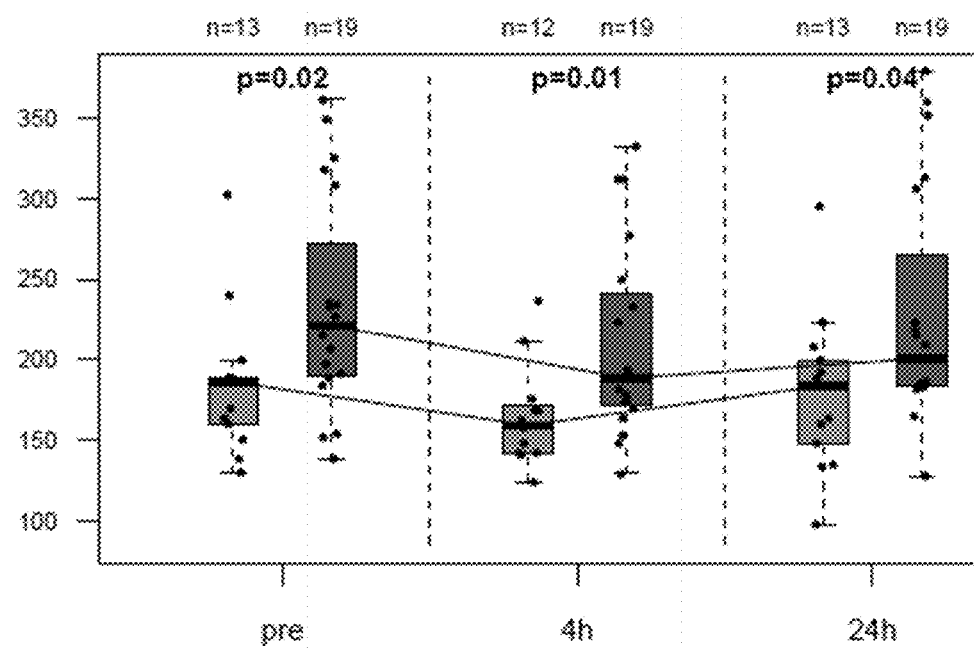
FIG. 2 IGFBP7 levels in cardiac surgery patients with preexisting CKD: Plasma levels of IGFBP7 were measured in 82 unselected adults undergoing cardiac surgery on the day before surgery as well as 4 and 24 hours after completion of CBP (which was defined as time point 0). Postoperative AKI within 3 days of surgery as defined by Acute Kidney Injury Network serum creatinine criteria were recorded within 3 days of surgery in 29 cases. Median IGFBP7 concentrations (ng/mL) at different times (pre-surgery, 4 and 24 hours after surgery) are provided for the subgroup with CKD with (n=19/32, black boxes) and without AKI (n=13/32, white boxes).
Figure 3:
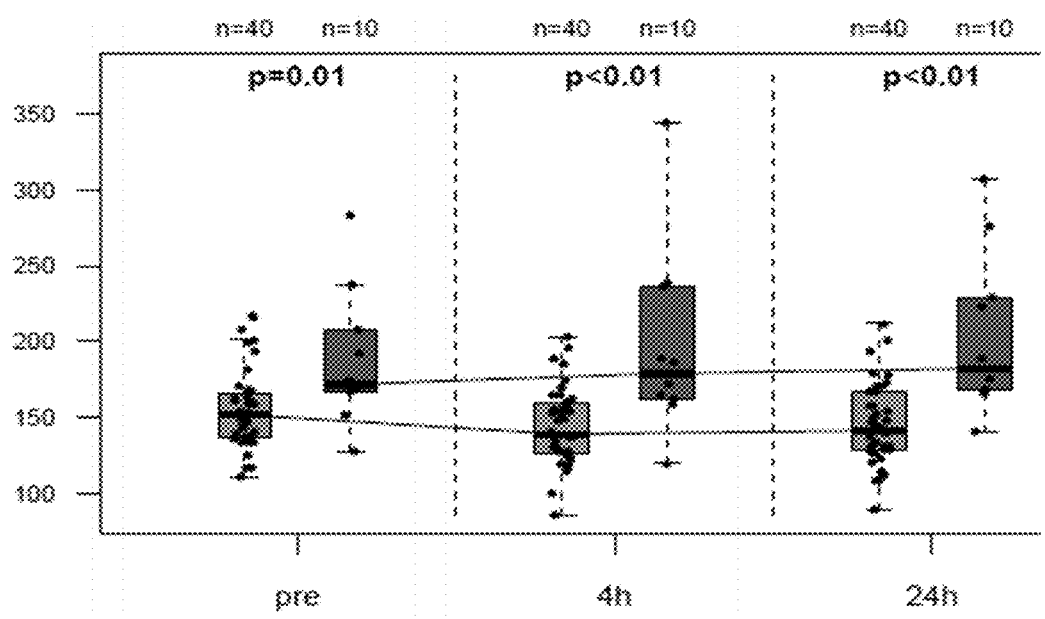
FIG. 3 IGFBP7 levels in cardiac surgery patients without preexisting CKD: Plasma levels of IGFBP7 were measured in 82 unselected adults undergoing cardiac surgery on the day before surgery as well as 4 and 24 hours after completion of CBP (which was defined as time point 0). Postoperative AKI within 3 days of surgery as defined by Acute Kidney Injury Network serum creatinine criteria were recorded within 3 days of surgery in 29 cases.

Conclusion:
IGFBP7 shows good prognostic performance within both subgroups of patients with or without preexisting chronic kidney disease (CKD) (FIGS. 2 and 3). Presurgery plasma IGFBP7 values have AUC close to 0.8 suggesting the association of IGFBP7 with the risk of developing AKI after surgery.

TABLE 2

CKD in the study cohort: Clinical characteristics of the study cohort is provided relating to subgroups of patients undergoing cardiac surgery with versus without preexisting chronic CKD.

| | No AKI | AKI | All |
|---|---|---|---|
| No preexisting CKD | n = 40 (80%) | n = 10 (20%) | n = 50 (100%) |
| Preexisting CKD | n = 13 (41%) | N = 19 (59%) | n = 32 (100%) |

Example 3

Combination of IGFBP7 with Other Biomarkers Selected from the Group of Creatinine, L-FABP, OPN, CysC, NGAL in Association with AKI in the Perioperative Setting The association of circulating plasma levels of IGFBP7, creatinine, L-FABP, OPN and CysC with AKI was investigated in patients undergoing cardiac surgery using cardiopulmonary bypass (CPB) at the University Hospital Erlangen. Patients with end stage renal disease, previous kidney transplantation and immunosuppressive medication were excluded. Biomarkers were measured in 82 unselected adults undergoing cardiac surgery on the day before surgery as well as 4 and 24 hours after completion of CBP (which was defined as time point 0). Postoperative AKI within 3 days of surgery as defined by Acute Kidney Injury Network serum creatinine criteria were recorded within 3 days of surgery in 29 cases. ROC curve analysis was performed using preoperative plasma IGFBP7, CysC, L-FABP, OPN and creatinine to predict AKI and had a c-statistic of 0.80, 0.74, 0.6, 0.67 and 0.66.

At 4 and 24 hours post-surgery IGFBP7, CysC, L-FABP, OPN, NGAL and creatinine had a c-statistics in their association with AKI of 0.83/0.85, 0.78/0.80, 0.73/0.82, 0.75/0.75, 0.71/0.78.

IGFBP7 had the best c-statistics of 0.8/0.83/0.85 at all investigated points in time of the perioperative setting in its association with AKI versus L-FABP, creatinine, OPN, NGAL and CysC.

In addition Table 3 demonstrates, that the c-statistics of all biomarkers is elevating over time in patients with AKI with the highest value (0.80) for IGFBP7 already at the preoperative sampling. CysC, creatinine, OPN, NGAL and L-FABP appear to behave roughly similar in terms of their kinetics in the setting of AKI.

Conclusion:
IGFBP7 c-statistics show good prognostic performance superior to all other investigated biomarkers before the surgery, as well as 4 h and 24 h after surgery.
Combination of IGFBP7 with biomarkers selected from the group of CysC, creatinine, OPN, NGAL and LFABP allows early (pre-surgery) risk prediction of AKI and provides additional kinetic information about the dynamics of stress in the perioperative setting.

TABLE 3

IGFBP7, pCrea, CysC, NGAL, OPN c-statistics to predict AKI in cardiac surgery patients over time: Plasma levels of IGFBP7, CysC, L-FABP, OPN and creatinine were measured in 82 unselected adults undergoing cardiac surgery on the day before surgery as well as 4 and 24 hours after completion of CBP (which was defined as time point 0). Postoperative AKI within 3 days of surgery as defined by Acute Kidney Injury Network serum creatinine criteria were recorded within 3 days of surgery in 29 cases. ROC curve analyses are provided for plasma IGFBP7, CysC, L-FABP, OPN, NGAL and creatinine measured at different points in time in the perioperative setting (preoperative sampling, 4 and 24 hours after surgery). Absolute values of c-statistics are provided as well as relative and absolute increases.

| | Absolute values | | | Relative increase AUC values | | Absolute increase | |
|---|---|---|---|---|---|---|---|
| | Pre | 4 h | 24 h | 4 h | 24 h | 4 h | 24 h |
| IGFBP7 | 0.80 | 0.83 | 0.85 | 0.57 | 0.66 | 0.51 | 0.62 |
| CysC | 0.74 | 0.78 | 0.80 | 0.52 | 0.70 | 0.63 | 0.70 |
| L-FABP | 0.60 | 0.73 | 0.82 | 0.65 | 0.74 | 0.71 | 0.73 |
| OPN | 0.67 | 0.75 | 0.75 | 0.56 | 0.59 | 0.63 | 0.70 |
| Creatinine | 0.66 | 0.71 | 0.78 | 0.60 | 0.82 | 0.57 | 0.84 |
| NGAL | 0.68 | 0.80 | 0.84 | 0.60 | 0.72 | 0.78 | 0.82 |

Example 4

Determination of IGFBP7 in Urine Samples of Patients Undergoing Surgery (Comparison Experiments)

Urinary IGFBP7 was determined in a subgroup of the patients described in Example 1. 34 patients were included in this study: 23 non-AKI, 9 AKI stage I, 1 AKI stage II, 1 AKI stage III. For each except 2 patients samples were drawn at three timepoints resulting in 102 measurements.

Urinary IGFBP7 was measured using the Nephro-Check®-Test from Astute Medical Inc (San Diego, Calif., USA). Measurements for determination of IGFBP7 concentration levels were done according to package insert. According to the package insert, the test is intended to be used in conjunction with clinical evaluation in patients who currently have or have had within the past 24 hours acute cardiovascular and or respiratory compromise and are ICU patients as an aid in the risk assessment for moderate or severe acute kidney injury (AKI) within 12 hours of patient assessment. The test predicts AKI based on a risk score which takes into account the level of urinary TIMP2 and urinary IGFBP7. However, assessment of urinary IGFBP7 concentrations independently of TIMP2 is possible as well. Therefore, the test could be used for comparative studies. The measurement of urine IGFBP7 and in the human urine samples was made using the Astute140® Meter.

For comparison experiments, Elecsys plasma IGFBP7 was determined in the same subgroup of 34 patients.

FIG. 4a shows the results for urinary IGFBP7, FIG. 4b shows the results for Elecsys plasma IGFBP7. The results are shown for samples obtained prior to surgery, and 4 hours and 24 hours after surgery in AKI (right boxplots) and non-AKI (left box-plots). Small black points indicate non-AKI patients or AKI stage I patients, larger points AKI stage II and III patients. The figure contains p-values of Wilcoxon test. Low p-values suggest significant difference of biomarker levels in the AKI and non-AKI groups.

As can be derived from FIG. 4b, the determination of IGFBP7 in plasma samples obtained prior to surgery allows for a reliable prediction of AKI in the analyzed subgroup (p<0.1). Advantageously, all forms of AKI, even mild form such as stage I, can be predicted

Example 5

Determination of IGFBP7 in Samples Obtained from Patients before Administration of a Contrast Medium The "acute chest pain study" included participants presenting with acute chest pain (>18 years). Exclusion criteria comprised pregnancy, preexisting AKI according to KDIGO or preexisting RRT. Retrospective biomarker analyses were performed in subgroups.

IGFBP7, CysC and creatinine are measured the subgroup of coronary angiography patients (comprising STEMI, Non-STEMI, UA) and correlated to contrast medium induced AKI vs. Non-AKI. Different contrast agents were used.

Plasma and urine samples obtained prior to administration of contrast medium (0h) and 12 hours later (12 h) are examined, (150 patients).

15 patients had developed AKI while 135 patients did not develop AKI. The same contrast media were administered to participants, that developed AKI, vs participants, that did not develop AKI.

The statistical calculation supports a minimum number of 15 AKI positive patients to be sufficient to detect biomarkers with an effect size corresponding to an AUC of 0.75. At least 15 AKI positive patients need to be in the biomarker substudy, assuming an event rate of 10%.

IGFBP7 and CysC are measured in plasma of 150 participants of the "acute chest pain study" obtained prior to administration of contrast medium. Median plasma IGFBP7 levels are compared with regard to association to the primary endpoint AKI vs. Non AKI. Altered IGFBP7 levels are observed in participants, that develop contrast medium induced AKI (n=15) vs those, that do not develop AKI (n=135).

Different patterns of IGFBP7 and CysC levels are observed. IGFBP7 levels observed are altered in samples obtained before administration of contrast medium in patients with contrast medium induced development of AKI. CysC levels show a high correlation to AKI stages.

Example 6

Determination of IGFBP7 in Samples of Patients Admitted to the ICU

Plasma levels of IGFBP7, Creatinine and CysC were measured in 67 patients at day 0, 1, 2, 3 and 7 after their arrival in the intensive care unit (ICU). The majority of patients developed sepsis. In summary 8 patients were found with no sepsis during their stay in the ICU, 11 patients with sepsis, 21 patients with severe sepsis and 27 patients with septic shock. The majority of patients developed AKI as defined by Acute Kidney Injury Network serum creatinine criteria. In summary 19 patients did not develop AKI, 9 patients developed AKI stage I, 8 patients developed AKI stage II and 31 patients developed AKI stage III. More than 70% of the patients with AKI stages II-III were found in subgroups with severe sepsis and septic shock.

FIG. 5 shows IGFBP7 levels obtained from ICU patients in the first samples taken after their inclusion in the study. The first sample was taken for the majority of patients at their arrival in the ICU or 1 day later.

Median IGFBP7 levels are provided for patient subgroups without sepsis, with sepsis, with severe sepsis and with septic shock divided by absence or presence of AKI stages II-III. ICU patients who developed AKI stages II-III were found to have significantly elevated plasma IGFBP7 levels in samples taken at the first point in time during their stay in the ICU versus non-AKI patients with same sepsis severity.

Moderate correlation between plasma IGFBP7 levels at visit 1 and AKI stages were observed within the whole collective (Spearman's correlation coefficient R=0.5, p<0.01) and within the patients with similar severity of sepsis. In contrast no correlation with sepsis stages was observed for IGFBP7 (Spearman's correlation coefficient R=0.26, p<0.01).

CysC showed stronger associations to AKI stages (Spearman's correlation coefficient R=0.67, p<0.01).

Different patterns of circulating IGFBP7 and CysC levels in plasma samples obtained at day 0, 1, 2, 3 and at day 7 after arrival in the ICU were observed for single patients. One patient developed severe septic shock and AKI stage III. IGFBP7 was found to be elevated one day before higher levels of Cystatine C or creatinine could be observed. IGFBP7 levels at day 0, 1, 2, 3 and 7 were: 462 ng/mL, 442 ng/mL, 337 ng/mL, 279 ng/mL and 335 ng/mL. CysC levels at day 0, 1, 2, 3 and 7 were: 1.55 µg/mL, 2.62 µg/mL, 2.91

µg/mL, 2.83 µg/mL and 3.43 µg/mL. Creatinin levels at day 0, 1, 2, 3 and 7 were: 0.92 mg/dL, 1.62 mg/dL, 1.86 mg/dL, 1.98 mg/dL and 0.99 mg/dL.

Conclusions:

As can be derived from FIG. 5, the determination of IGFBP7 in plasma samples obtained in the ICU allows a reliable prediction of AKI in patients with the same sepsis severity and in the whole group. Advantageously, all forms of AKI, as shown for stages II and III, can be predicted even in ICU patients with a high degree of inflammation and sepsis.

The determination of IGFBP7 in plasma samples obtained at arrival in the ICU or 1 day later allows for an early prediction of AKI in sepsis patients. Combination of IGFBP7 with CysC or creatinine allows early risk prediction of AKI at the first day after admission to the ICU and provides additional kinetic information about the dynamics of stress within the next week.

The invention claimed is:

1. A method for identifying a patient not at risk to suffer from acute kidney injury (AKI) during or after a surgical procedure or not at risk to suffer from acute kidney injury (AKI) after administration of a contrast medium and subjecting the identified patient to the surgical procedure or administering the contrast medium to the identified subject, comprising the steps of:
   (a) combining a blood, serum or plasma sample obtained from a patient prior to a surgical procedure or prior to administration of a contrast medium with an antibody specific for IGFBP7 (Insulin-like Growth Factor Binding Protein 7);
   (b) determining the amount of the biomarker IGFBP7 (Insulin-like Growth Factor Binding Protein 7) in the blood, serum or plasma sample obtained from the patient prior to the surgical procedure or prior to the administration of a contrast medium;
   (c) comparing the determined amount of said biomarker to a reference, wherein said reference is an amount of IGFBP7 in a patient or group of patients known to have suffered from acute kidney injury after a surgical procedure or after administration of a contrast medium;
   (d) identifying that the patient is not at risk of suffering from acute kidney injury during or after a surgical procedure or after administration of a contrast medium when the determined amount of IGFBP7 is below the reference; and
   (e) subjecting the identified patient to the surgical procedure or administering the contrast medium to the identified subject.

2. The method of claim 1, wherein said patient is a human patient.

3. The method of claim 1, wherein the patient is not an intensive care unit patient at the time at which the sample is obtained.

4. The method of claim 1, wherein the sample has been obtained within four weeks prior to said surgical procedure or the administration of the contrast medium.

5. The method of claim 1, wherein said reference is a predetermined value.

6. The method of claim 1, further comprising the determination of the amount of at least one additional biomarker selected from the group of Cystatin C, L-FABP (liver-type fatty acid binding protein), Osteopontin, IL-6 (Interleukin 6), NGAL, GDF-15 (Growth Differentiation Factor 15), Creatinine, a cardiac Troponin and a BNP-type peptide.

7. The method of claim 1, wherein the patient is suffering from chronic kidney disease.

8. The method of claim 1, wherein said surgical procedure is a surgery that involves general anesthesia, and/or mechanical ventilation.

9. The method of claim 1, wherein said surgical procedure is cardiac surgery.

10. The method of claim 1, wherein the sample has been obtained within one week prior to said surgical procedure or the administration of the contrast medium.

11. The method of claim 1, wherein the sample has been obtained within three days prior to said surgical procedure or the administration of the contrast medium.

12. The method of claim 1, wherein the sample has been obtained within 12 hours prior to said surgical procedure or the administration of the contrast medium.

* * * * *